US008841238B2

(12) United States Patent
Martineau et al.

(10) Patent No.: US 8,841,238 B2
(45) Date of Patent: Sep. 23, 2014

(54) METHODS FOR PRODUCING ACTIVE SCFV ANTIBODIES AND LIBRARIES THEREFOR

(75) Inventors: Pierre Emile Ulysse Martineau, Saint Gely du Fesc (FR); Etienne Weiss, Fegersheim (FR)

(73) Assignees: Institut National de la Sante et de la Recherche Medicale (INSERM), Paris (FR); Centre National de la Recherche Scientifique (C.N.R.S.), Paris (FR); Universite de Strasbourg, Strasbourg (FR)

(*) Notice: Subject to any disclaimer, the term of this patent is extended or adjusted under 35 U.S.C. 154(b) by 663 days.

(21) Appl. No.: 12/531,182

(22) PCT Filed: Mar. 17, 2008

(86) PCT No.: PCT/IB2008/000628
§ 371 (c)(1),
(2), (4) Date: Mar. 12, 2010

(87) PCT Pub. No.: WO2008/110914
PCT Pub. Date: Sep. 18, 2008

(65) Prior Publication Data
US 2010/0167957 A1 Jul. 1, 2010

Related U.S. Application Data

(60) Provisional application No. 60/894,947, filed on Mar. 15, 2007.

(51) Int. Cl.
*C40B 40/02* (2006.01)
*C40B 40/10* (2006.01)
*C07K 16/46* (2006.01)
*C07K 16/00* (2006.01)
*C12N 15/10* (2006.01)

(52) U.S. Cl.
CPC .......... *C12N 15/1034* (2013.01); *C07K 16/00* (2013.01); *C07K 2319/00* (2013.01); *C07K 2317/622* (2013.01); *C12N 15/1093* (2013.01); *C07K 2317/80* (2013.01); *C07K 2317/567* (2013.01)
USPC ........... 506/26; 506/18; 435/71.2; 530/387.3; 424/134.1

(58) Field of Classification Search
None
See application file for complete search history.

(56) References Cited

U.S. PATENT DOCUMENTS

| | | | |
|---|---|---|---|
| 5,565,332 A | 10/1996 | Hoogenboom et al. | |
| 5,858,657 A | 1/1999 | Winter et al. | |
| 7,258,986 B2 * | 8/2007 | Auf Der Maur et al. | 435/7.1 |
| 7,569,390 B1 * | 8/2009 | Eric et al. | 506/9 |
| 2004/0071696 A1 | 4/2004 | Adams et al. | |

FOREIGN PATENT DOCUMENTS

| | | |
|---|---|---|
| WO | 99/45959 | 9/1999 |
| WO | 00/54057 | 9/2000 |
| WO | 00/48017 | 7/2001 |
| WO | 03064611 A2 | 8/2003 |

OTHER PUBLICATIONS

Martineau et al., In vitro Folding and Tjhermodynamic Stability of an Antibody Fragment Selected in Vivo for High Expression Levels in *Escherichia coli* Cytoplasm, 1999, Journal of Molecular Biology, vol. 292, p. 921-929.*
Schier et al., Isolation of Picomolar Affinity Anti-c-erbB-2 Single-chain Fv by Molecular Evolution of Complementarity Determining Regions in the Center of the Antibody Binding Site, 1996, Journal of Molecular Biology, vol. 263, p. 551-567.*
Sblattero et al., Exploiting recombination in single bacteria to make large phage antibody libraries, Jan. 2000, Nature Biotechnology, vol. 18, p. 75-80.*
Visintin, Methods, vol. 34, p. 200-214, 2004.*
Lazar, Molecular and Cellular Biology, vol. 8, No. 3, p. 1247-1252, 1988.*
Burgess, The Journal of Cell Biology, vol. 111, p. 2129-2138, 1990.*
Jean-Charles Laden et a., "Expression and folding of an antibody fragment selected in vivo for high expression levels in *Escherichia coli* cytoplasm", Research in Microbiology Sep. 2002, vol. 153, No. 7 XP0025094241, ISSN: 0923-2508, pp. 469-474.
Sabine Jung et al., "Improving in vivo folding and stability of single-chain Fv antibody fragment by loop grafting", Protein Engineering, Oxford University Press, Surrey, GB, vol. 10, No. 8, Jan. 1, 1997, XP000971779, ISSN: 0269-2139, pp. 959-966.
Adrian Auf der Maur et al., "Antigen-independent selection of intracellular stable antibody frameworks", Methods (San Diego, Calif.) Oct. 2004, vol. 34, No. 2, XP004526807, ISSN: 1046-2023, pp. 215-224.
Adrian Auf der Maur et al., "Direct in Vivo Screening of Intrabody Libraries Constructed on a Highly Stable Single-chain Framework", The journal of Biological Chemistry 22, Nov. 2002, vol. 277, No. 47, XP002284890, ISSN: 0021-9258, pp. 45075-45085.
Pierre Martineau et al., "In vitro folding and Thermodynamic Stability of an Antibody Fragment Selected in Vivo for High Expression Levels in *Escherichia coli* Cytoplasm", Journal of Molecular Biology, London, GB, vol. 292, Oct. 1, 1999, XP004462583, ISSN: 0022-2836, pp. 921-929.
P. Martineau et al., "Expression of an Antibody Fragment at High Levels in the Bacterial Cytoplasm", Journal of Molecular Biology, London, GB, vol. 280, No. 1, Jul. 3, 1998, XP00453942, ISSN: 0022-2836, pp. 117-127.
Pascal Philibert et al., "A focused antibody library for selecting scFvs expressed at high levels in the cytoplasm", BMC Biotechnology 2007, vol., Nov. 22, 2007, XP002509301, ISSN: 1472-6760, p. 1-18.
International Search Report dated Jan. 16, 2009, from corresponding PCT application.

* cited by examiner

*Primary Examiner* — Misook Yu
*Assistant Examiner* — Michael D Allen
(74) *Attorney, Agent, or Firm* — Young & Thompson

(57) ABSTRACT

The present disclosure describes scFv antibody libraries, antibodies isolated from the libraries, and methods of producing and using the same.

6 Claims, 8 Drawing Sheets

SEQUENCE LISTING

<160> NUMBER OF SEQ ID NOS: 51

<210> SEQ ID NO 1
<211> LENGTH: 55
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (18)..(32)
<223> OTHER INFORMATION: n is a, c, g, or t

<400> SEQUENCE: 1
agggtgcctc tgccccannn nnnnnnnnnn nntctcacac agtaataaac agccg    55

<210> SEQ ID NO 2
<211> LENGTH: 58
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (18)..(35)
<223> OTHER INFORMATION: n is a, c, g, or t

<400> SEQUENCE: 2
agggtgcctc tgccccannn nnnnnnnnnn nnnnntctca cacagtaata aacagccg    58

```
<210> SEQ ID NO 3
<211> LENGTH: 61
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (18)..(38)
<223> OTHER INFORMATION: n is a, c, g, or t

<400> SEQUENCE: 3
agggtgcctc tgccccannn nnnnnnnnnn nnnnnnntc tcacacagta ataaacagcc    60
g                                                                  61

<210> SEQ ID NO 4
<211> LENGTH: 64
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (18)..(41)
<223> OTHER INFORMATION: n is a, c, g, or t

<400> SEQUENCE: 4
agggtgcctc tgccccannn nnnnnnnnn nnnnnnnnnn ntctcacaca gtaataaaca    60
gccg                                                               64

<210> SEQ ID NO 5
<211> LENGTH: 67
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (18)..(44)
<223> OTHER INFORMATION: n is a, c, g, or t

<400> SEQUENCE: 5
agggtgcctc tgccccannn nnnnnnnnn nnnnnnnnnn nnnntctcac acagtaataa    60
acagccg                                                            67

<210> SEQ ID NO 6
<211> LENGTH: 70
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (18)..(47)
<223> OTHER INFORMATION: n is a, c, g, or t

<400> SEQUENCE: 6
agggtgcctc tgccccannn nnnnnnnnn nnnnnnnnnn nnnnnntct cacacagtaa    60 taaacagccg                                                         70

<210> SEQ ID NO 7
<211> LENGTH: 73
<212> TYPE: DNA
<213> ORGANISM: Artificial Sequence
<220> FEATURE:
<223> OTHER INFORMATION: Synthetic Construct
<220> FEATURE:
```

```
<221> NAME/KEY: misc_feature
<222> LOCATION: (18)..(50)
<223> OTHER INFORMATION: n is a, c, g, or t

<400> SEQUENCE: 7
agggtgcctc tgccccannn nnnnnnnnnn nnnnnnnnnn nnnnnnnnnn tctcacacag    60
taataaacag ccg                                                     73

<210> SEQ ID NO 8
<211> LENGTH: 76
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (18)..(53)
<223> OTHER INFORMATION: n is a, c, g, or t

<400> SEQUENCE: 8
agggtgcctc tgccccannn nnnnnnnnnn nnnnnnnnnn nnnnnnnnnn nnntctcaca    60
cagtaataaa cagccg                                                  76

<210> SEQ ID NO 9
<211> LENGTH: 79
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (18)..(56)
<223> OTHER INFORMATION: n is a, c, g, or t

<400> SEQUENCE: 9
agggtgcctc tgccccannn nnnnnnnnnn nnnnnnnnnn nnnnnnnnnn nnnnnntctc    60
acacagtaat aaacagccg                                               79

<210> SEQ ID NO 10
<211> LENGTH: 82
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (18)..(59)
<223> OTHER INFORMATION: n is a, c, g, or t

<400> SEQUENCE: 10
agggtgcctc tgccccannn nnnnnnnnnn nnnnnnnnnn nnnnnnnnnn nnnnnnnnnt    60
ctcacacagt aataaacagc cg                                           82

<210> SEQ ID NO 11
<211> LENGTH: 85
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (18)..(62)
<223> OTHER INFORMATION: n is a, c, g, or t

<400> SEQUENCE: 11
agggtgcctc tgccccannn nnnnnnnnnn nnnnnnnnnn nnnnnnnnnn nnnnnnnnnn    60
```
nntctcacac agtaataaac agccg    85

<210> SEQ ID NO 12
<211> LENGTH: 88
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (18)..(65)
<223> OTHER INFORMATION: n is a, c, g, or t

<400> SEQUENCE: 12
agggtgcctc tgcccannn nnnnnnnnn nnnnnnnnn nnnnnnnnn    60 nnnnntctca cacagtaata aacagccg    88

<210> SEQ ID NO 13
<211> LENGTH: 91
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (18)..(68)
<223> OTHER INFORMATION: n is a, c, g, or t

<400> SEQUENCE: 13
agggtgcctc tgcccannn nnnnnnnnn nnnnnnnnn nnnnnnnnn    60 nnnnnnnntc tcacacagta ataaacagcc g    91

<210> SEQ ID NO 14
<211> LENGTH: 67
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (23)..(49)
<223> OTHER INFORMATION: n is a, c, g, or t

<400> SEQUENCE: 14
ggacgaggct gattattact gcnnnnnnnn nnnnnnnnn nnnnnnnnt tcggcggagg    60 gaccaag    67

<210> SEQ ID NO 15
<211> LENGTH: 70
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (23)..(52)
<223> OTHER INFORMATION: n is a, c, g, or t

<400> SEQUENCE: 15
ggacgaggct gattattact gcnnnnnnnn nnnnnnnnn nnnnnnnnn nttcggcgg    60 agggaccaag    70

<210> SEQ ID NO 16
<211> LENGTH: 67
<212> TYPE: DNA

```
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (23)..(49)
<223> OTHER INFORMATION: n is a, c, g, or t

<400> SEQUENCE: 16
ggacgaggct gattattact gcnnnnnnnn nnnnnnnnnn nnnnnnnnnt tcggcggagg      60
gaccaag                                                               67

<210> SEQ ID NO 17
<211> LENGTH: 70
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (23)..(52)
<223> OTHER INFORMATION: n is a, c, g, or t

<400> SEQUENCE: 17
ggacgaggct gattattact gcnnnnnnnn nnnnnnnnnn nnnnnnnnnn nnttcggcgg      60
agggaccaag                                                            70

<210> SEQ ID NO 18
<211> LENGTH: 73
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (23)..(55)
<223> OTHER INFORMATION: n is a, c, g, or t

<400> SEQUENCE: 18
ggacgaggct gattattact gcnnnnnnnn nnnnnnnnnn nnnnnnnnnn nnnnnttcgg      60
cggagggacc aag                                                        73

<210> SEQ ID NO 19
<211> LENGTH: 20
<212> TYPE: DNA
<213> ORGANISM: Artificial Sequence
<220> FEATURE:
<223> OTHER INFORMATION: Synthetic Construct

<400> SEQUENCE: 19
ccggatatag ttcctccttt                                                 20

<210> SEQ ID NO 20
<211> LENGTH: 20
<212> TYPE: DNA
<213> ORGANISM: Artificial Sequence
<220> FEATURE:
<223> OTHER INFORMATION: Synthetic Construct

<400> SEQUENCE: 20
ctgctaacca gtaaggcaac                                                 20

<210> SEQ ID NO 21
<211> LENGTH: 24
<212> TYPE: DNA
<213> ORGANISM: Artificial Sequence
```

-continued

```
<220> FEATURE:
<223> OTHER INFORMATION: Synthetic Construct

<400> SEQUENCE: 21
gagcggataa caatttcaca cagg                                           24

<210> SEQ ID NO 22
<211> LENGTH: 23
<212> TYPE: DNA
<213> ORGANISM: Artificial Sequence
<220> FEATURE:
<223> OTHER INFORMATION: Synthetic Construct

<400> SEQUENCE: 22
agggttttcc cagtcacgac gtt                                            23

<210> SEQ ID NO 23
<211> LENGTH: 20
<212> TYPE: DNA
<213> ORGANISM: Artificial Sequence
<220> FEATURE:
<223> OTHER INFORMATION: Synthetic Construct

<400> SEQUENCE: 23
aacggtggta tatccagtga                                                20

<210> SEQ ID NO 24
<211> LENGTH: 23
<212> TYPE: DNA
<213> ORGANISM: Artificial Sequence
<220> FEATURE:
<223> OTHER INFORMATION: Synthetic Construct

<400> SEQUENCE: 24
cggtggtata tccagtgatt ttt                                            23

<210> SEQ ID NO 25
<211> LENGTH: 17
<212> TYPE: DNA
<213> ORGANISM: Artificial Sequence
<220> FEATURE:
<223> OTHER INFORMATION: Synthetic Construct

<400> SEQUENCE: 25
tggggcagag gcaccct                                                   17

<210> SEQ ID NO 26
<211> LENGTH: 17
<212> TYPE: DNA
<213> ORGANISM: Artificial Sequence
<220> FEATURE:
<223> OTHER INFORMATION: Synthetic Construct

<400> SEQUENCE: 26
agggtgcctc tgcccca                                                   17

<210> SEQ ID NO 27
<211> LENGTH: 22
<212> TYPE: DNA
<213> ORGANISM: Artificial Sequence
<220> FEATURE:
<223> OTHER INFORMATION: Synthetic Construct

<400> SEQUENCE: 27
gcagtaataa tcagcctcgt cc                                             22
```

<210> SEQ ID NO 28
<211> LENGTH: 32
<212> TYPE: DNA
<213> ORGANISM: Artificial Sequence
<220> FEATURE:
<223> OTHER INFORMATION: Synthetic Construct

<400> SEQUENCE: 28
taaggcggcc gcaatggaga aaaaaatcac tg         32

<210> SEQ ID NO 29
<211> LENGTH: 22
<212> TYPE: DNA
<213> ORGANISM: Artificial Sequence
<220> FEATURE:
<223> OTHER INFORMATION: Synthetic Construct

<400> SEQUENCE: 29
actgccttaa aaagcttacg cc         22

<210> SEQ ID NO 30
<211> LENGTH: 31
<212> TYPE: DNA
<213> ORGANISM: Artificial Sequence
<220> FEATURE:
<223> OTHER INFORMATION: Synthetic Construct

<400> SEQUENCE: 30
actgataagc ttgccaccat ggccgaggtg c         31

<210> SEQ ID NO 31
<211> LENGTH: 31
<212> TYPE: DNA
<213> ORGANISM: Artificial Sequence
<220> FEATURE:
<223> OTHER INFORMATION: Synthetic Construct

<400> SEQUENCE: 31
ttgattacta gtgagttttt gttctgcggc c         31

<210> SEQ ID NO 32
<211> LENGTH: 819
<212> TYPE: DNA
<213> ORGANISM: Artificial Sequence
<220> FEATURE:
<223> OTHER INFORMATION: Synthetic Construct

<400> SEQUENCE: 32
atggccgagg tgcagctggt ggagtctggg ggaagcctgg tcaagcctgg ggggtccctg         60
agactctcct gtgcagcctc tggattcacc ttcagtaact atagcatgaa ctgggtccgc        120
caggctccag ggaagggct ggagtggatc tcatccatta gtggtagtag tagatacata        180
tactacgcag acttcgtgaa gggccgattc accatctcca gagacaacgc cacgaactca        240
ctgtacctgc aaatgaacag cctgagagcc gaggacacgg ctgtttatta ctgtgtgaga        300
tccagtatta cgattttttgg tggcggtatg gacgtctggg gcagaggcac cctggtcacc        360
gtctcctcag gtggaggcgg ttcaggcgga gtggcagcg cggtggcgg atcgcagtct        420 gtgctgactc agcctgcctc cgtgtctggg tctcctggac agtcgatcac catctcctgc        480
gctggaacca gcagtgacgt tggtggttat aactatgtct cctggtacca acaacccca        540 ggcaaagccc ccaaactcat gatttatgag gacagtaagc ggccctcagg ggtttctaat        600
cgcttctctg gctccaagtc tggcaacacg gcctccctga caatctctgg gctccaggct        660

```
gaggacgagg ctgattatta ctgcagctca tatacaacca ggagcactcg agttttcggc    720
ggagggacca agctggccgt cctaggtgcg gccgcagaac aaaaactcat ctcagaagag    780
gatctgaatg gggccgcaca tcaccatcat caccattaa                           819
```

<210> SEQ ID NO 33
<211> LENGTH: 272
<212> TYPE: PRT
<213> ORGANISM: Artificial Sequence
<220> FEATURE:
<223> OTHER INFORMATION: Synthetic Construct

<400> SEQUENCE: 33

```
Met Ala Glu Val Gln Leu Val Glu Ser Gly Gly Ser Leu Val Lys Pro
1               5                   10                  15

Gly Gly Ser Leu Arg Leu Ser Cys Ala Ala Ser Gly Phe Thr Phe Ser
            20                  25                  30

Asn Tyr Ser Met Asn Trp Val Arg Gln Ala Pro Gly Lys Gly Leu Glu
        35                  40                  45

Trp Ile Ser Ser Ile Ser Gly Ser Ser Arg Tyr Ile Tyr Tyr Ala Asp
    50                  55                  60

Phe Val Lys Gly Arg Phe Thr Ile Ser Arg Asp Asn Ala Thr Asn Ser
65                  70                  75                  80

Leu Tyr Leu Gln Met Asn Ser Leu Arg Ala Glu Asp Thr Ala Val Tyr
                85                  90                  95

Tyr Cys Val Arg Ser Ser Ile Thr Ile Phe Gly Gly Gly Met Asp Val
            100                 105                 110

Trp Gly Arg Gly Thr Leu Val Thr Val Ser Ser Gly Gly Gly Gly Ser
        115                 120                 125

Gly Gly Gly Gly Ser Gly Gly Gly Gly Ser Gln Ser Val Leu Thr Gln
    130                 135                 140

Pro Ala Ser Val Ser Gly Ser Pro Gly Gln Ser Ile Thr Ile Ser Cys
145                 150                 155                 160

Ala Gly Thr Ser Ser Asp Val Gly Gly Tyr Asn Tyr Val Ser Trp Tyr
                165                 170                 175

Gln Gln His Pro Gly Lys Ala Pro Lys Leu Met Ile Tyr Glu Asp Ser
            180                 185                 190

Lys Arg Pro Ser Gly Val Ser Asn Arg Phe Ser Gly Ser Lys Ser Gly
        195                 200                 205

Asn Thr Ala Ser Leu Thr Ile Ser Gly Leu Gln Ala Glu Asp Glu Ala
    210                 215                 220

Asp Tyr Tyr Cys Ser Ser Tyr Thr Thr Arg Ser Thr Arg Val Phe Gly
225                 230                 235                 240

Gly Gly Thr Lys Leu Ala Val Leu Gly Ala Ala Ala Glu Gln Lys Leu
                245                 250                 255

Ile Ser Glu Glu Asp Leu Asn Gly Ala Ala His His His His His His
            260                 265                 270
```

<210> SEQ ID NO 34
<211> LENGTH: 12
<212> TYPE: PRT
<213> ORGANISM: Artificial Sequence
<220> FEATURE:
<223> OTHER INFORMATION: Synthetic Construct

<400> SEQUENCE: 34

Ser Ser Ile Thr Ile Phe Gly Gly Gly Met Asp Val

```
1               5                   10
```

<210> SEQ ID NO 35
<211> LENGTH: 9
<212> TYPE: PRT
<213> ORGANISM: Artificial Sequence
<220> FEATURE:
<223> OTHER INFORMATION: Synthetic Construct

<400> SEQUENCE: 35

```
His Ser Arg Glu Val His Arg Thr Phe
1               5
```

<210> SEQ ID NO 36
<211> LENGTH: 8
<212> TYPE: PRT
<213> ORGANISM: Artificial Sequence
<220> FEATURE:
<223> OTHER INFORMATION: Synthetic Construct

<400> SEQUENCE: 36

```
Ser Gly Gly Asn Thr Phe Asp Tyr
1               5
```

<210> SEQ ID NO 37
<211> LENGTH: 9
<212> TYPE: PRT
<213> ORGANISM: Artificial Sequence
<220> FEATURE:
<223> OTHER INFORMATION: Synthetic Construct

<400> SEQUENCE: 37

```
Gln Gln Tyr Tyr Arg Lys Pro Trp Thr
1               5
```

<210> SEQ ID NO 38
<211> LENGTH: 14
<212> TYPE: PRT
<213> ORGANISM: Artificial Sequence
<220> FEATURE:
<223> OTHER INFORMATION: Synthetic Construct

<400> SEQUENCE: 38

```
Gly Asn Ala Asp Gly Gly Glu Asn Trp Glu Leu Phe Asp Lys
1               5                   10
```

<210> SEQ ID NO 39
<211> LENGTH: 9
<212> TYPE: PRT
<213> ORGANISM: Artificial Sequence
<220> FEATURE:
<223> OTHER INFORMATION: Synthetic Construct

<400> SEQUENCE: 39

```
Gln Leu Tyr Gln Asn Thr Leu Trp Thr
1               5
```

<210> SEQ ID NO 40
<211> LENGTH: 12
<212> TYPE: PRT
<213> ORGANISM: Artificial Sequence
<220> FEATURE:
<223> OTHER INFORMATION: Synthetic Construct

<400> SEQUENCE: 40

```
Ser Ser Ile Thr Ile Phe Gly Gly Gly Met Asp Val
1               5                   10
```

<210> SEQ ID NO 41
<211> LENGTH: 9
<212> TYPE: PRT
<213> ORGANISM: Artificial Sequence
<220> FEATURE:
<223> OTHER INFORMATION: Synthetic Construct

<400> SEQUENCE: 41

Gln Gln Asn Trp Thr Ser Pro Leu Ser
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic Construct

<400> SEQUENCE: 42

Arg Gly Arg Asp Tyr
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic Construct

<400> SEQUENCE: 43

Gln Gln Tyr Asn Thr Ser Pro Phe Ser
1               5

<210> SEQ ID NO 44
<211> LENGTH: 7
<212> TYPE: PRT
<213> ORGANISM: Artificial Sequence
<220> FEATURE:
<223> OTHER INFORMATION: Synthetic Construct

<400> SEQUENCE: 44

Gly Arg Asn Val Leu Asn Tyr
1               5

<210> SEQ ID NO 45
<211> LENGTH: 10
<212> TYPE: PRT
<213> ORGANISM: Artificial Sequence
<220> FEATURE:
<223> OTHER INFORMATION: Synthetic Construct

<400> SEQUENCE: 45

Gln Gln Asn Ser Ser Ser Pro Arg Phe Thr
1               5                   10

<210> SEQ ID NO 46
<211> LENGTH: 7
<212> TYPE: PRT
<213> ORGANISM: Artificial Sequence
<220> FEATURE:
<223> OTHER INFORMATION: Synthetic Construct

<400> SEQUENCE: 46

Gly Arg Arg Ala Leu Gly Asn
1               5

```
<210> SEQ ID NO 47
<211> LENGTH: 9
<212> TYPE: PRT
<213> ORGANISM: Artificial Sequence
<220> FEATURE:
<223> OTHER INFORMATION: Synthetic Construct

<400> SEQUENCE: 47

Gln Gln Tyr Asn Thr Ser Pro Phe Ser
1               5

<210> SEQ ID NO 48
<211> LENGTH: 7
<212> TYPE: PRT
<213> ORGANISM: Artificial Sequence
<220> FEATURE:
<223> OTHER INFORMATION: Synthetic Construct

<400> SEQUENCE: 48

Gly Arg Arg Ala Leu Gly Asn
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic Construct

<400> SEQUENCE: 49

Leu Thr Trp Ser Met Arg Ser Ala Ile
1               5

<210> SEQ ID NO 50
<211> LENGTH: 7
<212> TYPE: PRT
<213> ORGANISM: Artificial Sequence
<220> FEATURE:
<223> OTHER INFORMATION: Synthetic Construct

<400> SEQUENCE: 50

Gly Arg Arg Ala Leu Gly Asn
1               5

<210> SEQ ID NO 51
<211> LENGTH: 11
<212> TYPE: PRT
<213> ORGANISM: Artificial Sequence
<220> FEATURE:
<223> OTHER INFORMATION: Synthetic Construct

<400> SEQUENCE: 51

Leu Thr Thr Glu Asn Ser Val Tyr Arg Leu Val
1               5                   10
```

US 8,841,238 B2

METHODS FOR PRODUCING ACTIVE SCFV ANTIBODIES AND LIBRARIES THEREFOR

FIELD

This disclosure relates to recombinant single-chain antibodies and methods of producing and using such antibodies.

BACKGROUND

Genetic engineering approaches have allowed the production of recombinant antibodies having specific binding specificities, specific domain structures, and other desirable properties. One type of genetically engineered antibody is the single chain Fv fragment (scFv). Single chain Fv fragments are genetically engineered polypeptides that contain a heavy chain variable region (VH) linked to a light chain variable region (VL) via a flexible peptide linker. Each VH and VL domain contains three complementarity determining regions (CDRs). CDRs are short amino acid sequences that vary greatly among antibody molecules, and thus, are responsible for generating the great diversity of antibody binding specificity. The combination of the CDRs of the VH plus the CDRs of the VL determines the binding specificity of any given antibody.

Single chain Fv fragments display the binding specificity and monovalent binding affinity of full-size antibodies and provide the added benefit of relative ease of genetic manipulation and expression (because scFvs are encoded by and expressed from a single coding sequence, rather than from separate coding sequences, as are full-size antibodies). Single chain Fv fragments and other recombinant antibodies are used in a broad variety of applications, for example, in medical diagnostic tests, in basic research, and as therapeutic antibody treatments for various diseases.

Intrabodies are genetically-engineered antibody molecules that are ectopically expressed within cells. Intrabodies can be used to visualize or to modulate the function of a target antigen within living cells. For example, the use of intrabodies can induce a phenotypic knockout either by directly inhibiting the function of the targeted antigen or by diverting the targeted antigen from its normal intracellular location (e.g., an intrabody can redirect its target antigen to the degradation machinery). Intrabodies can also enhance or change the function of their target antigens. For protein targets, intrabodies can be targeted to a specific post-translational modification or to a specific antigen conformation. Moreover, an intrabody-induced phenotypic knockout can be confined to a specific cell compartment by targeting an intrabody to the specific subcellular compartment using an addressing signal (e.g., a nuclear localization signal, a mitochondrial localization signal, or an endoplasmic reticulum retention signal). Intrabodies can also modulate target function by modifying the oligomeric structure of the target.

Because intrabody phenotypic knockout relies only on the binding capacity of the antibody molecule to its target, it is not necessary to express within the cell a complete antibody molecule but only its binding site, which is entirely located within the variable region (Fv). Given their advantages of small size and antigen specificity encompassed within a single polypeptide chain, scFvs are the most common type of recombinant antibody fragment used for intracellular antibody expression.

One serious limitation to the use of intrabodies is that most scFvs are not able to fold under the reducing conditions of the cell cytosol and nucleus. Under such conditions the two conserved disulfide bridges of scFvs are reduced, thereby destabilizing and inactivating the binding activity of many scFvs. In vitro, most scFvs cannot be renatured under reducing conditions. Statistical analyses of scFv sequences have shown that fewer than 1% of the scFvs are stable enough to be expressed and active in absence of disulfide bond formation. In addition, even if a scFv protein is indeed stable enough in its reduced form to be expressed and active in vivo, other parameters such as protease susceptibility or folding kinetics may also influence the final in vivo fate of the intrabody and thus are critical for ultimate intrabody expression and activity.

To obtain an active intrabody, current approaches often involve two successive steps. First, a panel of scFv or Fab antibodies that specifically bind an antigen of interest are identified (for example, by screening a phage display library). Second, the specifically-binding antibodies are tested for their ability to bind and/or inhibit the target antigen in vivo. Because fewer than 1% of scFvs are potentially useful as intrabodies (because they are not expressed and/or cannot properly fold under the reducing conditions that exist within a cell), identification of a single scFv that can be used as an intrabody requires the isolation of more than 100 scFv clones, a number that is unlikely to be obtained in most cases.

In view of the foregoing difficulties in producing and identifying antibodies that can be used as intrabodies for use in medical and research applications, what is needed are more efficient methods of producing and selecting antibodies that can be used as intrabodies.

SUMMARY

In a first aspect, described herein is an antibody library that includes at least about $10^6$ unique scFv clones, wherein at least about 20% of the scFv clones encode an antibody that can detectably specifically bind a target antigen within a cell when the antibody encoded by the scFv clone is expressed within the cell.

In a second aspect, described herein is an antibody library, wherein the antibody library includes at least about $10^6$ unique scFv antibody clones, wherein at least about 20% of the scFv antibody clones can be expressed within an *E. coli* cell to produce soluble antibody at a level of at least about 5 mgs per liter of *E. coli* cells, wherein the *E. coli* cells have been grown to an $OD_{600nm}$ of about 5.

In a third aspect, described herein is an antibody library including at least about $10^6$ unique scFv antibody clones, wherein each unique scFv antibody clone encodes a unique scFv antibody comprising at least one of a unique CDR3 VH sequence and a unique CDR3 VL sequence, and wherein the unique scFv antibody clones encode a framework sequence substantially identical to a framework sequence encoded by scFv13R4.

In any of the above antibody libraries, the unique scFv antibody clones can encode scFv antibodies including a unique CDR3 VH sequence.

In any of the above antibody libraries, the unique scFv antibody clones can encode scFv antibodies including a unique CDR3 VL sequence.

In any of the above antibody libraries, the unique scFv antibody clones can encode scFv antibodies including a unique CDR3 VH sequence and a unique CDR3 VL sequence.

In a fourth aspect, described herein is an scFv antibody that can be expressed as substantially soluble protein under reducing conditions, wherein the scFv antibody is isolated from the library described above in the third aspect. The scFv antibody can specifically bind to a target antigen under reducing conditions.

In a fifth aspect, described herein is a method of producing an scFv antibody, including expressing the scFv antibody described above in the fourth aspect within a cell, thereby producing the scFv antibody. The method can include further purifying the scFv antibody from the cell.

In a sixth aspect, described herein is a method for preparing an scFv antibody library enriched for scFv antibody clones that can be expressed within a cell, including: a) providing a first collection of scFv antibody clones, wherein the first collection comprises clones comprising a unique sequence within a CDR3 loop of VH, wherein the first collection has been enriched for scFv antibody clones that can be detectably expressed when introduced into a cell; b) providing a second collection of scFv antibody clones, wherein the second collection comprises clones comprising a unique sequence within a CDR3 loop of VL, wherein the second collection has been enriched for scFv antibody clones that can be detectably expressed when introduced into a cell; c) joining VH domains from scFv antibody clones of the first collection with VL domains from scFv antibody clones of the second collection to obtain a third collection of scFv antibody clones, wherein the third collection contains scFv antibody clones comprising a unique sequence within the CDR3 loop of VH and a unique sequence within the CDR3 loop of VL, thereby preparing the scFv antibody library enriched for scFv antibody clones that can be expressed within a cell.

In the above method for preparing an scFv antibody library, the first collection can include scFv antibody clones that contain a substantially identical VL sequence relative to other scFv antibody clones in the first collection, and the second collection can include scFv antibody clones that contain a substantially identical VH sequence relative to other scFv antibody clones in the second collection.

In the above method for preparing an scFv antibody library, the first collection can include scFv antibody clones that contain a VL sequence substantially identical to an scFv13R4 VL sequence and the second collection can include scFv antibody clones that contain a VH sequence substantially identical to an scFv13R4 VH sequence.

In the above method for preparing an scFv antibody library, the first collection can include scFv antibody clones that include identical CDR1 and CDR2 sequences in the VH domain and the second collection can include scFv antibody clones that include identical CDR1 and CDR2 sequences in the VL domain.

In a seventh aspect, described herein is an antibody library produced by the method described above in the sixth aspect.

In an eighth aspect, described herein is an antibody selected from an antibody library produced by the method described above in the sixth aspect.

In a ninth aspect, the invention features a method for constructing an antibody library including: a) selecting an scFv antibody framework; b) introducing sequence diversity into a VH CDR3 region of the scFv antibody framework to generate a first library including scFv antibody clones including a unique VH CDR3 region; c) introducing sequence diversity into a VL CDR3 region of the scFv antibody framework to generate a second library including scFv antibody clones including a unique VL CDR3 region; d) removing, from the first library, clones that do not detectably express scFv antibody; e) removing, from the second library, clones that do not detectably express scFv antibody; and f) recombining the first and second libraries to generate a final library comprising scFv antibody clones comprising a unique VH CDR3 region and a unique VL CDR3 region, thereby constructing the antibody library.

In the above method, the scFv can be scFv13R4.

It is an object of the present invention to provide a novel antibody library for the isolation of scFvs expressed in the cytoplasm that may be used as intrabodies.

It is another object of the present invention to provide a novel antibody library based on a single framework and optimized for intracellular expression.

A further object of the present invention is to provide novel methods of constructing and validating a novel antibody library for the isolation of scFvs expressed in the cytoplasm that may be used as intrabodies.

Another object of the present invention is to provide novel methods of constructing and validating a novel antibody library based on a single framework and optimized for intracellular expression.

Still another object of the present invention is to provide novel methods of using an antibody library in order to produce highly expressed scFvs that may be used as intrabodies.

Yet another object of the present invention is to provide novel methods of using an antibody library in order to produce scFvs based on a single framework and optimized for intracellular expression.

These and other objects, features, and advantages of the present invention will become apparent after review of the following detailed description of the disclosed embodiments.

DETAILED DESCRIPTION OF THE INVENTION

Figure 1:
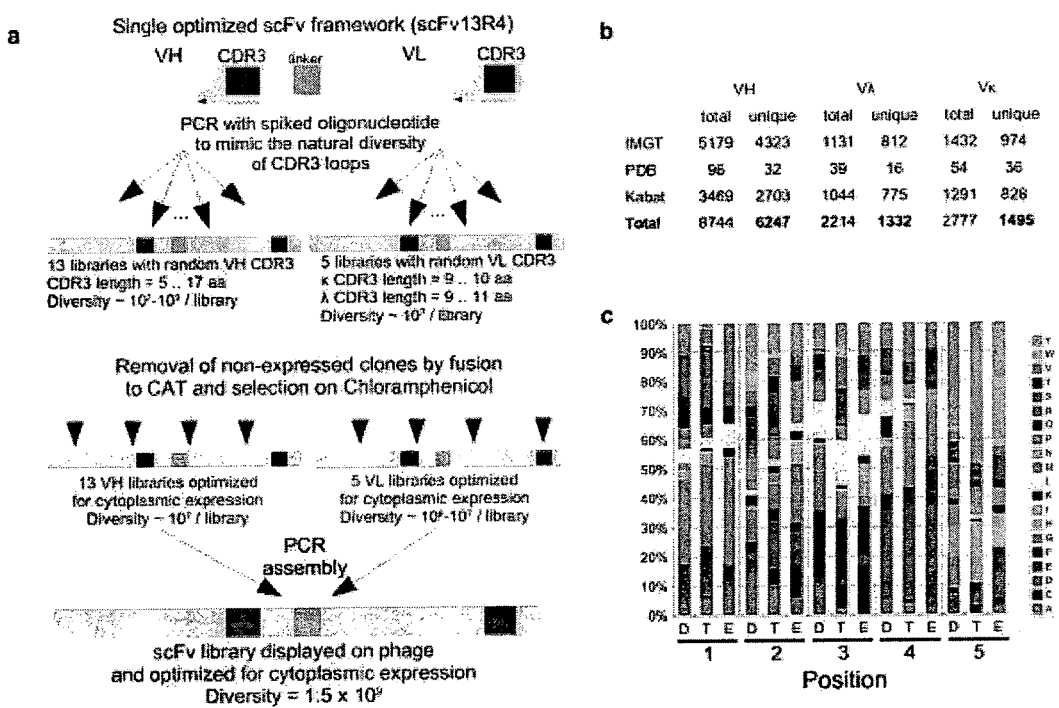
FIG. 1. (a) Schematic outline of the steps followed during library construction. The critical steps are: introduction of tailored CDR3 loops in an unique human scFv framework; removal of non-expressed clones by fusion with the CAT enzyme and selection on CAM plates; recombination of the 13 VH and 5 VL libraries, and display on phage. (b) Summary of the CDR3 loops collected in the database. (c) Distribution of the amino acids at each position of the 5 amino acid long VH CDR3s from 55 rearranged human antibodies.
Figure 2:
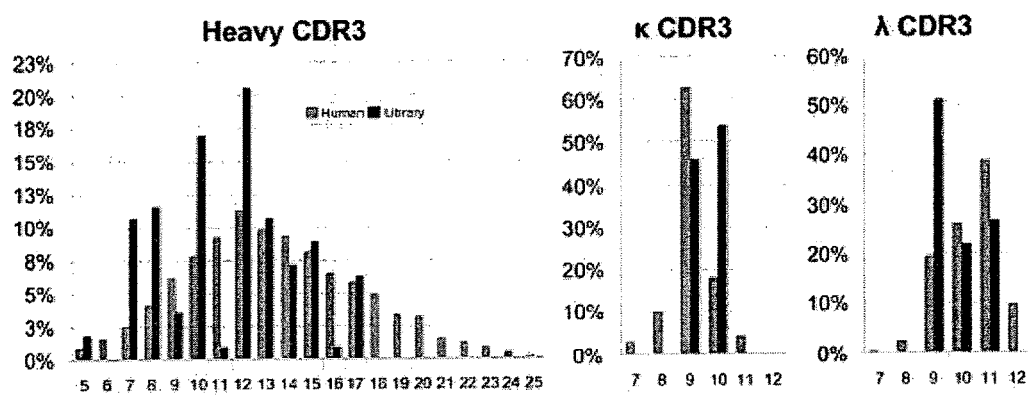
FIG. 2. Schematic representation of CDR3 length distribution. Distribution of the CDR3 lengths in the database and in 118 sequenced clones from the library.

Provided herein are methods for constructing an scFv library enriched for scFvs that can be expressed within a prokaryotic or eukaryotic cell. The scFvs maintain their structure under the reducing conditions present within a cell, retain their ability to specifically bind a target antigen within a cell, and thus can be used as intrabodies in various therapeutic and research approaches. Because the methods described herein can be used to produce libraries of scFvs that are stable under reducing conditions, these libraries are also useful for producing scFvs that can be expressed by and purified from prokaryotic or eukaryotic cells (e.g., by lysing the cells and purifying the desired scFv by well-known techniques). Such purified scFvs are useful as antibodies for use in research, diagnostic tests, and for disease therapies.

An improved strategy for stabilizing scFvs to be used in vivo is to construct a scFv library tailored for intracellular expression. Ideally, such a library should only contain scFvs able to fold under reducing conditions such as those found in the cytoplasm of a cell. Another strategy is to construct an scFv library based on a single optimized antibody framework for intrabody selection.

Described herein are methods for constructing a novel antibody library that is based on a single optimized antibody framework and tailored for intracellular expression. Through molecular evolution, we obtained a human scFv called scFv13R4, which is expressed at high levels in E. coli cytoplasm. In addition, this scFv is highly expressed, soluble, and displays specific binding activity to a target antigen in yeast and mammalian cells. This scFv is very stable in vitro and can be renatured in presence of a reducing agent. In addition, analysis of its folding kinetics showed that it folds faster than the parent scFv and aggregates more slowly in vitro.

The human scFv library based on the framework of the optimized scFv13R4 contains more than a billion clones, which is larger than previous libraries of $10^7$ to $10^8$. The diversity of the present human scFv library is much greater than that of previous libraries because we designed the present library to encode VH and VL CDR3 loops of various different lengths. In addition, we used a biased mix of degenerate oligonucleotide sequences to encode CDR3 loops that mimic human CDR3. Using optimized CDR3 loops and filtering steps to eliminate the non-expressed clones, we purged the library of non-expressed scFvs and retained the cytoplasmically expressed scFvs without compromising the diversity of the clones, as confirmed through testing with several proteins used as the antigens. Contrary to previously described scFv libraries, most of the scFvs in the library are well expressed in E. coli and in mammalian cytoplasm.

This new approach to building scFv libraries allows facile and large-scale selection of functional intrabodies. For example, several strong binders against different proteins, including the Syk and Auroroa-A protein kinases, the αβ tubulin dimer, the papillomavirus E6 proteins, the core histones, gankyrin, and MAPK11-14, have been isolated from the library. Some of the selected scFvs are expressed at an exceptionally high level in the bacterial cytoplasm, allowing the purification of 1 mg or more of active scFv from only 20 ml of culture. Moreover, after three rounds of selection against core histones as a target antigen, more than half of the selected scFvs were active when expressed in vivo in human cells and were essentially localized in the nucleus. This new type of library, methods of creating and using such libraries, and antibodies isolated from such libraries, are useful not only for the simple and large-scale selection of functional intrabodies but also for the expression and purification of highly expressed scFvs that can be used in numerous biotechnological, diagnostic, and therapeutic applications.

Intrabodies

Intrabodies are genetically-engineered antibody molecules that are ectopically expressed within cells. Intrabodies can be used to visualize or to inhibit a targeted antigen in living cells, and thus find use in various research and medical (e.g., diagnostic and therapeutic) applications. However, intrabody technology has been limited by the fact that fewer than 1% scFvs in a typical antibody expression library are stable enough to be expressed and/or active in vivo, because the intracellular environment reduces the two conserved disulfide bridges that the vast majority of scFvs require for stability. Described herein are methods of producing libraries of scFvs that are greatly enriched for scFvs that are stable under reducing conditions and thus are suitable for use as intrabodies. The intrabodies can be used for various research, diagnostic, and therapeutic approaches that employ intrabodies.

In most cases, obtaining efficient intrabodies currently requires two successive steps. First, a panel of antibodies against the target antigen must be isolated. Due to the availability of very high quality naive antibody libraries displayed on phage, this step is now easily accomplished by phage-display and can be automated in order to isolate binders against several proteins in parallel. In a second step, these antibody fragments (scFv or Fab) must be tested in vivo for their ability to inhibit their target. However, most scFvs do not fold properly under the reducing conditions found in the cytosol and the nucleus of the cell where most of the interesting targets are located. This can result in aggregated and inactive scFvs, which are unable to interact with their target. Since less than 1% of scFvs are efficient as intrabodies, getting a single binder against a protein requires the isolation of 100 different scFvs, a number which is unlikely to be obtained in most cases. This makes the process of identifying intrabodies from regular scFv libraries a difficult procedure even when the screening is done in vivo using two-hybrid or equivalent systems. In addition, this low proportion of active scFvs in the current libraries results in a 100-fold decrease in the potential repertoire screened, making the isolation of intrabodies against different epitopes of the same protein unlikely.

Libraries

Described herein are novel phage-display libraries of scFvs optimized for intracellular expression and novel methods of constructing and using the library. The library is constructed on a single antibody framework of a parental scFv which was selected because of its improved activity inside the cytoplasm. The parental scFv is very stable, has favorable folding and aggregation kinetics and is expressed at very high levels in all tested cell types. Having a single framework for the construction of a library should allow more comparable expression levels between clones since most of their sequences are conserved.

Because CDR sequences also play a role in scFv folding and expression, however, we believed that the expression level of the clones would still exhibit some variability. To minimize these differences, we introduced variability only within the CDR3 loops because these loops are the most variable in antibodies and are thus more likely to be highly tolerant to sequence and length variations. Introduction of variability in the CDR3 is sufficient to generate antibodies against most proteins. In addition, we carefully biased the frequencies of the amino acids in these loops so as to recover the distribution observed among natural human sequences. When the expression levels of randomly selected clones were compared in the cytoplasm, despite some clear differences, a high proportion of them were correctly expressed both in $E.$ $coli$ and in mammalian cells. This proportion of intracellularly expressed scFvs is much higher than in previously described libraries.

We were also able to select binders (i.e., antibodies that specifically bind to a selected target antigen) against five different proteins (Aurora-A, GST:Syk, tubulin, histones, and E6 protein from papillomavirus HPV16). In subsequent studies we have also isolated binders against new targets including gankyrin and MAPK11-14. For MAPK11-14, the four proteins involved are the four isoforms of the p38 MAP kinase. These proteins are very homologous (~60-74% identity). In all cases we were able to isolate scFvs specific for the isoform used for the selection. This underlines the specificity of the scFvs that can be isolated from this library.

A frequent concern when constructing scFv libraries is the simultaneous optimization of the library's diversity and size. Generally, the size of such a library is limited by the transformation efficiency to about $10^{10}$ clones. Given this limited number of clones, it is thus of premium importance to avoid non-expressed scFvs or duplicates. To solve this problem we first selected an antibody framework that was already optimized for intracellular expression, and then used a two-step procedure to further optimize the library.

First, we constructed 18 "small" libraries for each CDR3 length (13 VH CDR3 lengths and 5 VL CDR3 lengths) to be used for constructing the scFv library (see Example 1, herein below). Each of these 18 libraries was made by replacing the corresponding CDR3 of the parental scFv13R4 by the randomized CDR3. The resulting library with one and only one randomized CDR3 was then fused to the gene encoding chloramphenicol acetyltransferase (CAT), which we used as a selectable marker. After transformation of each CDR3 library into $E.$ $coli$, the libraries were plated on chloramphenicol (CAM)-containing medium to select for those CDR3-CAT fusions that were expressed in the $E.$ $coli$ cytoplasm. This step reduced the diversity of each library by about 10-30%.

Although the CAT gene is used in the examples provided herein, one of ordinary skill in the art will understand that nucleic acids encoding any appropriate selectable marker can be fused with CDR3-encoding-nucleic acids and used in the methods provided herein to enrich scFv libraries for scFvs that are expressed in prokaryotic or eukaryotic cells. For example, suitable selectable markers for use in bacterial cells include, but are not limited to, the kanamycin resistance gene. Examples of selectable markers for use in mammalian cells include but are not limited to, e.g., the neomycin resistance gene, the puromycin resistance gene, and the hygromycin resistance gene. Examples of selectable markers for yeast cells include URA3, HIS3, and purE. In addition, markers such as green fluorescent protein (GFP) and derivatives thereof, beta-galactosidase, luciferase, or other luminescent, fluorometric, and/or colorimetric markers can be used, in all types of cells, for example, with fluorescence-activated cell sorting (FACS), to enrich scFv libraries for clones that encode scFvs that are capable of being expressed. One of ordinary skill in the art will understand how to use the teachings herein, together with what is known in the art, to select an appropriate selectable marker and an appropriate selection scheme to construct the scFv libraries described herein.

In a second step, we used PCR to randomly assemble the selected VH and VL libraries to generate the final diversity, based on the hypothesis that if a newly-generated scFv clone containing a new CDR3 sequence in its VH region plus the original VL of scFv13R4 was expressed, and if a newly-generated scFv clone containing a new CDR3 sequence in its VL region plus the original VH region of scFV13R4 was expressed, then a recombined scFv clone containing the new CDR3 sequence in its VH region plus the new CDR3 sequence in its VL region would also be expressed, thereby resulting in a library containing only expressed scFvs. This was the case since 19 out of 20 clones selected at random were expressed at least partially in a soluble form in $E.$ $coli$ cytoplasm. Importantly, since this selection step was done early during the library construction, the diversity of the final library was only limited by the final transformation. This final recombination step, by generating a high diversity, ensured that all the clones were unique in the final library. Altogether, this approach resulted in a library of 1.5 billion expressed and different scFvs.

Successful use of scFvs as intrabodies on a large scale requires several essential points to be fulfilled by the library. First, the scFv must be easy to isolate. This is the case for the presently-described methods, since not only were we able to isolate binders against all the tested proteins, but also a single cycle of selection was enough to get close to 100% of binders. This very high enrichment rate is presumably due both to the high quality of the biased library which contains only well expressed scFvs and to the use of the trypsin-sensitive helper phage KM13. This is of premium importance since it may be possible to use a single panning cycle before in vivo testing of the scFvs as intrabodies, allowing a better diversity of the targeted epitopes. Also, this high enrichment rate also reduces by a huge amount the quantity of purified antigen needed for the panning steps. We were able to select on microtiter plates with as little as 1 µg of protein per well. Since further selection and confirmation of the binding activity by ELISA is not necessary because of the very high proportion of binders, it is now possible to isolate good intrabodies with a very small amount of antigen. Second, the scFv should be able to fold in all the cell compartments, particularly in the reducing ones such as the cytoplasm and the nucleus. Again, this is the case for the scFv library described herein, since more than 80% of the tested clones are at least partially soluble in the cell. In addition, we have shown that good cytoplasmic binders can be obtained from the phage selected scFvs in *E. coli* and in eukaryotic cells.

Provided herein are antibody libraries that comprises at least about: $10^6$, $5 \times 10^6$, $10^7$, $5 \times 10^7$, $10^8$, $5 \times 10^8$, $10^9$, $1.5 \times 10^9$, $5 \times 10^9$, $10^{10}$, $5 \times 10^{10}$, $10^{11}$, $5 \times 10^{11}$, $10^{12}$, $10^{13}$, $10^{14}$, $10^{15}$, or $10^{16}$ unique scFv clones, wherein at least about: 20%, 30%, 40%, 50%, 60%, 70%, 80%, 85%, or more of the scFv clones encode an antibody that can detectably specifically bind a target antigen when the antibody encoded by the scFv clone is expressed within a cell (e.g., as an intrabody). The scFvs described herein can be expressed to detectably specifically bind to a target antigen in any prokaryotic or eukaryotic cell in which it would be desirable to detectably specifically bind a target antigen (e.g., but not limited to, a bacterial cell, a yeast cell, an insect cell, an amphibian cell, an avian cell, a mammalian cell, and the like).

By "specifically binds" is meant that an scFv antibody preferentially binds to its target antigen rather than to another antigen. By "detectably specifically binds" is meant that specific binding of scFv antibody to its target antigen can be observed, e.g., but not limited to a phenotypic change in the cell in which the scFv antibody binds to its target antigen, or detection of the interaction between the scFv antibody and its target antigen (e.g., co-localization of the scFv antibody and its target antigen within a cell).

Exemplary Uses

Though the libraries described herein have been optimized for the isolation of intrabodies, the libraries can also be used to select scFvs for diagnostic and therapeutic applications. Furthermore, because we designed the CDR3 diversity using expressed human sequences, the scFvs present in the library are fully human and should not induce an anti-scFv antibody response in patients.

The libraries described herein and the antibodies produced by it are useful not only for identifying functional intrabodies but also for the isolation of highly expressed scFvs that could be used in numerous biotechnological and therapeutic applications. For example, the library and the antibodies produced by it may be have uses related to or including, but not limited to, gene delivery strategies therapeutic agents, drug discovery tools, counteracting agglutination of unwanted target molecules, combating disease states relating to misfolded protein disorders, and binding, neutralizing, or modifying the function of a cancer-related target.

For example, the intrabodies described herein can be used to modulate the activity of syk tyrosine kinase and other proteins implicated in allergic disorders (see, e.g., WO2005106481; see also Ulanova et al., Expert Opin Ther Targets 2005, 9:901-921. MAP kinases (MAPK) are key mediators of cell proliferation and are often targeted for inhibition in cancer therapy (see, e.g., Sebolt-Leopold J S and Herrera, R, Nat Rev Cancer, 4:937-947 (2004)) Other interesting targets are microtubules and associated proteins (see Jordan M A and Wilson, L, Nat Rev Cancer, 4:253-265 (2004)).

Immunobodies can be used to treat or prevent diseases in commercially valuable plants, such as crops, e.g., using the methods described in Villani, M E et al. Immunomodulation of cucumber mosaic virus infection by antibodies selected in vitro from a stable single-framework phage display library, Plant Molecular Biology 58(3):305 (2005)).

The intrabodies described herein can be used to treat, or prevent infections in human or animal cells. For example, intrabodies can be used to treat, ameliorate, or prevent infection of cells by the human immunodeficiency virus, using methods as described, for example, in Swan, C H et al, T-cell protection and enrichment through lentiviral CCR5 gene delivery, Gene Ther. 13:1480-1492.

The intrabodies described herein can be used to target proteins involved in neurological disorders, e.g., as described, e.g., in Miller, T W et al (A human single-chain Fv intrabody preferentially targets amino-terminal Huntingtin's fragments in striatal models of Huntington's disease, Neurobiol dis. 19:47-56 (2005)) and Miller and Messer (Intrabody applications in neurological disorders: progress and future prospects, Mol. Ther. 12:394-401 (2005).

The intrabodies described herein can be used for cancer therapy by targeting a protein involved in cancer like oncoproteins, as described, e.g., in Williams, B R and Zhu, Z (Intrabody-based approaches to cancer therapy: status and prospects, Current med Chem 13:1473-1480 (2006) and Doorbar J. and Griffin H. (2007) Intrabody strategies for the treatment of human papillomavirus-associated disease. Expert Opin. Biol. Ther. 7(5), 677-689.

The intrabodies described herein can be used to treat infections (e.g. but not limited to Epstein-Barr Virus) by targeting a protein expressed by an infectious agent, e.g., as described in Fang C Y et al (Modulation of Epstein0-Barr Virus Latent Membrane Protein 1 Activity by Intrabodies, Intervirology 50:254-263 (2007)

As described herein, an intrabody can be administered to a cell by administering to the cell an expression vector encoding the intrabody of interest. Expression vectors that are suitable for expression of intrabodies are well-known in the art. Administration of expression vectors that encode the intrabodies described herein, can be achieved by any one of numerous, well-known approaches, for example, but not limited to, direct transfer of the nucleic acids, in a plasmid or viral expression vector, alone or in combination with carriers such as cationic liposomes. Such expression vectors (which contain promoter and enhancer sequences suitable for expressing an operably-linked coding sequence when the expression vector is introduced into a cell) and methods for making, using, and delivering such vectors to cells are well known in the art and readily adaptable for use for administering intrabodies to cells.

Vectors can be any nucleotide construction used to deliver genes into cells, e.g., a plasmid or viral vector, such as a retroviral vector which can package a recombinant retroviral genome (see e.g., Pastan et al., Proc. Natl. Acad. Sci. U.S.A. 85:4486, 1988; Miller et al., Mol. Cell. Biol. 6:2895, 1986). The recombinant retrovirus can then be used to infect and thereby deliver a nucleic acid of the invention to the infected cells. The exact method of introducing the altered nucleic acid into mammalian cells is, of course, not limited to the use of retroviral vectors. Other techniques are widely available for this procedure including the use of adenoviral vectors (Mitani et al., Hum. Gene Ther. 5:941-948, 1994), adeno-associated viral (AAV) vectors (Goodman et al., Blood 84:1492-1500, 1994), lentiviral vectors (Naidini et al., Science 272:263-267, 1996), pseudotyped retroviral vectors (Agrawal et al., Exper. Hematol. 24:738-747, 1996). Physical transduction techniques can also be used, such as liposome delivery and receptor-mediated and other endocytosis mechanisms (see, for example, Schwartzenberger et al., Blood 87:472-478, 1996). This invention can be used in conjunction with any of these or other commonly used gene transfer methods. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991).

Cell-permeable intrabodies (transbodies) can be administered to cells by fusing an scFv antibody with a protein transduction domain (PTD) that allows the cell-permeable intrabody to cross the cell membrane and enter the cell, for example, according to the methods described in Heng, B C and Cao, T (Making cell-permeable antibodies (Transbody) through fusion of protein transduction domains (PTD) with single chain variable fragment (scFv) antibodies: potential advantages over antibodies expressed within the intracellular environment (Intrabody), Med Hypotheses 64:1105-1108 (2005)). Alternatively, the scFv could be mixed with cationic lipids and delivered efficiently into cells, as shown with complete antibodies (Courtête J., Sibler A. P., Zeder-Lutz G., Dalkara D., Zuber G. & Weiss E. (2007) Suppression of cervical carcinoma cell growth by intracytoplasmic co-delivery of anti-oncoprotein E6 antibody and siRNA. *Mol. Cancer. Ther.* 6, 1728-36). Such cell-permeable intrabodies can be used in cell culture (e.g., for research purposes) and for diagnostic purposes (e.g., to detect a virus or microorganism in sample of cells from a human, animal, or plant suspected of harboring an infectious agent. Such cell-permeable intrabodies can be administered to research animals (e.g. but not limited to systemic administration, e.g., by intravenously administering an intrabody to a research animal, or by topical administration, for example) to modulate the activity of a particular target antigen and thereby alter a phenotype in the animal. Such cell-permeable intrabodies can also be administered to human or non-human animal patients to treat or prevent disease or infection as described above. For example, cell-permeable intrabodies can be administered intravenously, topically, orally, or by other well-known methods, as will be appreciated by one of ordinary skill in the art.

Use of the Present scFv Antibodies for Large-Scale Antibody Production

Because the scFv antibody clones encode antibodies that fold under reducing conditions, the libraries described herein are also useful for identifying scFv antibodies that can be produced in large quantities by expressing the scFv antibodies in cells (e.g., prokaryotic cells such as bacterial cells, or eukaryotic cells such as yeast cells, insect cells, mammalian cells, or the like) and isolating the scFv antibodies from the cells. Single chain scFv antibodies for which it would be desirable to purify large quantities of antibody include but are not limited to, for example, scFv antibodies that are useful in laboratory research, for medical diagnostic tests, for commercial diagnostic tests or other types of diagnostic tests (e.g., to detect contaminating microorganisms in drinking water or food), and for antibody therapeutics (e.g., to treat cancer or to treat infectious or other types of diseases in which an antibody can be used to treat the disease).

Provided herein are antibody libraries for the isolation of expressed scFv antibodies, wherein the antibody library comprises at least about: $10^6$, $5 \times 10^6$, $10^7$, $5 \times 10^7$, $10^8$, $5 \times 10^8$, $10^9$, $1.5 \times 10^9$, $5 \times 10^9$, $10^{10}$, $5 \times 10^{10}$, $10^{11}$, $5 \times 10^{11}$, $10^{12}$, $10^{13}$, $10^{14}$, $10^{15}$, or $10^{16}$ unique scFv antibody clones, wherein at least about: 20%, 25%, 30%, 35%, 40%, 50%, 55%, 60%, 65%, 70%, 75%, 80%, 70 or more than 80% of the scFv antibody clones can be expressed within a cell to produce soluble antibody at a level of at least about: 5 mgs, 8 mgs, 10 mgs, 15 ms, 20 mgs, 25 mgs, 30 mgs, 35 mgs, 40 mgs, 45 mgs, 50 mgs, or more than 50 mgs per liter of cells in a flask grown to an $OD_{600nm}$ of about 5.

There are many well-accepted approaches for expressing and purifying proteins such as expressed scFv antibodies from cells and one of ordinary skill in the art will understand how to select the most appropriate type of cell expression system from which to express and purify scFv antibodies. Many manuals that describe methods for protein expression are known in the art. See, e.g., Current Protocols in Molecular Biology, John Wiley and Sons, 2006.

Definitions

By "unique sequence" is meant that, within a collection of scFv antibody clones, there are at least $10^6$ clones that contain a CDR3 sequence that is different from the CDR3 sequences of other clones within the collection of scFv antibody clones. With reference to an scFv antibody clone or a library of such clones, a "unique sequence" is different from the sequence present at the corresponding position within scFv13R4.

The terms "antibody framework" and "framework sequence" refer to any non-unique portion of the scFv antibody clones, e.g., any portion of the scFv antibody that is not a unique CDR3 VH region and/or unique CDR3 VL region. As referred to herein, the antibody framework or framework sequence is that of scFv13R4, the parental scFv clone upon which the present libraries are based.

By "substantially identical" is meant that two or more amino acid sequences being compared are at least 98%, 98.5%, 99%, or 99.5% the same, or that two or more nucleic acid sequences being compared encode amino acid sequences that are at least 98%, 98.5%, 99%, or 99.5% the same.

By "common sequence" is meant a nucleotide or amino acid sequence that is shared among scFv clones.

By "scFv antibody clone" is meant a nucleic acid molecule that encodes an individual species of scFv antibody that comprises a unique sequence within the VH CDR3 domain, the VL CDR3 domain, or within both VH and VL CDR3 domains.

By "target antigen" is meant an antigen that is preferentially bound by a particular antibody, compared to the binding of that particular antibody to another antigen that is not a target antigen.

By "specifically binds" binds is meant that an antibody strongly and preferentially binds to a particular target antigen, compared to the binding of the antibody to other antigens.

By "ectopically expressed" is meant that expression of an antibody of interest is not naturally expressed within a particular type of cell in which the antibody is being expressed, i.e., the antibody is expressed within the cell because an expression construct encoding the antibody has been introduced into the cell.

By "isolated" or "purified" is meant that an scFv antibody has been substantially separated, produced apart from, or purified away from other biological components in the cell in which it has been produced, that is, substantially separated away from other cellular components, such as other cellular proteins, DNA, RNA, lipids, and the like. The term "isolated" or "purified" does not require absolute purity; rather, it is intended as a relative term. Preferably, an scFv antibody is purified or isolated away from other cellular components such that the scFv antibody represents at least: 25%, 30%, 40%, 50%, 60%, 70% 80%, 90%, 95%, or greater, of the total content of the scFv antibody preparation.

By "soluble" antibody means that an antibody molecule is not in aggregate form. A soluble antibody has the ability to specifically bind its target antigen.

By "substantially soluble" is mean that at least 20%, e.g., at least 25%, 30%, 40%, 50%, 60%, 70%, 80%, or more of an scFv antibody as described herein is properly folded and thus can specifically bind its target antigen.

Example 1

Construction of an scFv Library Optimized for Intracellular Expression

Materials

Bacterial Strains, Chemicals and Enzymes

LB and 2xYT media were previously described (Miller, J. H. *A Short Course in Bacterial Genetics: a Laboratory Manual and Handbook for Escherichia coli and Related Bacteria*. Cold Spring Harbor Laboratory Press; 1992). Strain C-Max5F' (Bio-rad laboratories) is *E. coli* K-12, [F' lacI$^q$ Tn10] φ80dlacZΔM15 Δ(lacZYA-argF)U169 recA1 endA1 hsdR17($r_k^-$ $m_k^+$) phoA supE44λ-thi-1 gyrA96 relA1. MC1061 (ATCC #53338) is *E. coli* K-12, F-λ-hsdR2 hsdM+ hsdS+mcrA mcrB1 araD139 Δ(ara-leu)7696 Δ(lacIPOZY) X74 galE15 galU galK16 rpsL thi. Non-suppressor strain HB2151 is *E. coli* K-12 [F'proA$^+$B$^+$ lacI$^q$ lacZΔM15] ara Δ(lac-pro) thi. Chemicals were purchased from Sigma. Restriction enzymes and cloned Taq polymerase were from Fermentas. ProofStart and Pfu DNA polymerases were respectively purchased from Qiagen and Promega. Plasmid DNA, PCR and agarose-separated DNA were purified using Macherey-Nagel Nucleospin kits.

Oligonucleotides

Eighteen spiked oligonucleotides used to introduce degenerate CDR3 loops were synthesized and purified using high-pressure liquid chromatography (HPLC) by IBA GmbH (Goettingen, Germany). The sequences of the 18 spiked oligonucleotides is as follows. H3_n=n amino acid long VH CDR3 loop; K3_n=n amino acid long VL kappa (K) CDR3 loop; L3_n=n amino acid long VL lambda (λ) CDR3 loop. For the degenerate positions, the percentages of the 4 bases are given as N(A/C/G/T). The proportions of each nucleotide used at each spiked (degenerate) position is shown in Table 1 below.

H3_5:
(SEQ ID NO: 1)
AGGGTGCCTCTGCCCCANNNNNNNNNNNNNNNNNTCTCACACAGTAATAAAC
AGCCG;

H3_6:
(SEQ ID NO: 2)
AGGGTGCCTCTGCCCCANNNNNNNNNNNNNNNNNNNNTCTCACACAGTAATA
AACAGCCG;

H3_7:
(SEQ ID NO: 3)
AGGGTGCCTCTGCCCCANNNNNNNNNNNNNNNNNNNNNNNTCTCACACAGTA
ATAAACAGCCG;

H3_8:
(SEQ ID NO: 4)
AGGGTGCCTCTGCCCCANNNNNNNNNNNNNNNNNNNNNNNNNNTCTCACACA
GTAATAAACAGCCG;

H3_9:
(SEQ ID NO: 5)
AGGGTGCCTCTGCCCCANNNNNNNNNNNNNNNNNNNNNNNNNNNNNTCTCAC
ACAGTAATAAACAGCCG;

H3_10:
(SEQ ID NO: 6)
AGGGTGCCTCTGCCCCANNNNNNNNNNNNNNNNNNNNNNNNNNNNNNNTCT
CACACAGTAATAAACAGCCG;

H3_11:
(SEQ ID NO: 7)
AGGGTGCCTCTGCCCCANNNNNNNNNNNNNNNNNNNNNNNNNNNNNNNNNNN
TCTCACACAGTAATAAACAGCCG;

H3_12:
(SEQ ID NO: 8)
AGGGTGCCTCTGCCCCANNNNNNNNNNNNNNNNNNNNNNNNNNNNNNNNNN
NNNTCTCACACAGTAATAAACAGCCG;

H3_13:
(SEQ ID NO: 9)
AGGGTGCCTCTGCCCCANNNNNNNNNNNNNNNNNNNNNNNNNNNNNNNNNN
NNNNNNTCTCACACAGTAATAAACAGCCG;

H3_14:
(SEQ ID NO: 10)
AGGGTGCCTCTGCCCCANNNNNNNNNNNNNNNNNNNNNNNNNNNNNNNNNN
NNNNNNNNNTCTCACACAGTAATAAACAGCCG;

H3_15:
(SEQ ID NO: 11)
AGGGTGCCTCTGCCCCANNNNNNNNNNNNNNNNNNNNNNNNNNNNNNNNNN
NNNNNNNNNNNNTCTCACACAGTAATAAACAGCCG;

H3_16:
(SEQ ID NO: 12)
AGGGTGCCTCTGCCCCANNNNNNNNNNNNNNNNNNNNNNNNNNNNNNNNNN
NNNNNNNNNNNNNNNTCTCACACAGTAATAAACAGCCG;

H3_17:
(SEQ ID NO: 13)
AGGGTGCCTCTGCCCCANNNNNNNNNNNNNNNNNNNNNNNNNNNNNNNNNN
NNNNNNNNNNNNNNNNNNTCTCACACAGTAATAAACAGCCG;

K3_9:
(SEQ ID NO: 14)
GGACGAGGCTGATTATTACTGCNNNNNNNNNNNNNNNNNNNNNNNNNNNT
TCGGCGGAGGGACCAAG;

K3_10:
(SEQ ID NO: 15)
GGACGAGGCTGATTATTACTGCNNNNNNNNNNNNNNNNNNNNNNNNNNNNN
NNTTCGGCGGAGGGACCAAG;

L3_9:
(SEQ ID NO: 16)
GGACGAGGCTGATTATTACTGCNNNNNNNNNNNNNNNNNNNNNNNNNNNT
TCGGCGGAGGGACCAAG;

L3_10:
(SEQ ID NO: 17)
GGACGAGGCTGATTATTACTGCNNNNNNNNNNNNNNNNNNNNNNNNNNNNN
NNTTCGGCGGAGGGACCAAG;

L3_11:
(SEQ ID NO: 18)
GGACGAGGCTGATTATTACTGCNNNNNNNNNNNNNNNNNNNNNNNNNNNNN
NNNNNTTCGGCGGAGGGACCAAG.

TABLE 1

H3_5
(SEQ ID NO: 1)
AGGGTGCCTCTGCCCCA N(40/5/50/5) N(5/5/5/85) N(60/5/25/10) N(40/10/45/5)

N(15/30/5/50) N(5/75/10/10) N(30/35/30/5) N(50/20/10/20) N(60/20/5/15)

N(30/25/40/5) N(15/20/25/40) N(35/40/5/20) N(25/50/20/5) N(10/50/10/30)

N(5/55/35/5) TCTCACACAGTAATAAACAGCCG

H3_6
(SEQ ID NO: 2)
AGGGTGCCTCTGCCCCA N(55/5/35/5) N(10/5/5/80) N(75/15/5/5) N(45/5/45/5)

N(5/10/10/75) N(5/85/5/5) N(45/35/15/5) N(55/20/10/15) N(55/20/10/15)

N(40/30/25/5) N(10/40/15/35) N(25/45/5/25) N(45/30/20/5) N(15/40/20/25)

N(10/35/30/25) N(20/15/60/5) N(10/60/10/20) N(5/70/10/15)

TCTCACACAGTAATAAACAGCCG

H3_7
(SEQ ID NO: 3)
AGGGTGCCTCTGCCCCA N(35/5/55/5) N(15/5/15/65) N(65/15/10/10)

N(55/5/35/5) N(5/5/5/85) N(5/85/5/5) N(50/5/40/5) N(75/5/10/10) N(60/10/20/10)

N(10/45/40/5) N(15/35/25/25) N(25/55/5/15) N(35/35/25/5) N(10/45/15/30)

N(25/45/15/15) N(25/25/25/25) N(20/40/15/25) N(10/35/25/30) N(40/15/40/5)

N(5/50/15/30) N(5/80/10/5) TCTCACACAGTAATAAACAGCCG

H3_8
(SEQ ID NO: 4)
AGGGTGCCTCTGCCCCA N(55/5/35/5) N(10/5/10/75) N(75/10/5/10) N(50/5/40/5)

N(5/5/5/85) N(5/85/5/5) N(45/5/45/5) N(75/5/10/10) N(65/5/20/10) N(25/45/25/5)

N(10/25/40/25) N(30/45/5/20) N(55/10/30/5) N(5/55/15/25) N(5/55/15/25)

N(35/35/25/5) N(15/45/20/20) N(15/40/10/35) N(30/40/25/5) N(20/35/20/25)

N(15/40/20/25) N(65/5/20/10) N(15/45/5/35) N(5/70/15/10)

TCTCACACAGTAATAAACAGCCG

H3_9
(SEQ ID NO: 5)
AGGGTGCCTCTGCCCCA N(40/5/50/5) N(10/5/10/75) N(75/5/15/5) N(40/5/50/5)

N(5/5/5/85) N(5/85/5/5) N(45/5/45/5) N(85/5/5/5) N(70/5/15/10) N(55/25/15/5)

N(10/25/35/30) N(35/45/15/5) N(10/25/60/5) N(10/35/20/35) N(20/45/15/20)

N(30/30/35/5) N(15/40/20/25) N(20/40/15/25) N(65/20/10/5) N(20/40/20/20)

N(5/45/15/35) N(15/30/50/5) N(20/45/20/15) N(5/40/25/30) N(30/25/40/5)

N(10/40/10/40) N(5/60/20/15) TCTCACACAGTAATAAACAGCCG

H3_10
(SEQ ID NO: 6)
AGGGTGCCTCTGCCCCA N(50/5/40/5) N(20/5/10/65) N(70/10/15/5) N(60/5/30/5)

N(5/5/5/85) N(5/85/5/5) N(35/5/55/5) N(85/5/5/5) N(75/5/15/5) N(30/35/30/5)

N(10/20/45/25) N(30/45/15/10) N(30/35/30/5) N(5/30/20/45) N(30/40/10/20)

N(40/35/20/5) N(15/35/25/25) N(25/35/15/25) N(50/30/15/5) N(10/45/20/25)

N(20/50/10/20) N(25/20/50/5) N(20/40/20/20) N(5/50/15/30) N(20/20/40/20)

N(20/35/20/25) N(5/35/30/30) N(5/30/60/5) N(15/35/10/40) N(5/60/15/20)

TCTCACACAGTAATAAACAGCCG

TABLE 1-continued

H3_11
(SEQ ID NO: 7)
AGGGTGCCTCTGCCCCA N(55/5/35/5) N(10/5/10/75) N(80/5/10/5) N(60/5/30/5)

N(5/5/5/85) N(5/85/5/5) N(45/5/45/5) N(85/5/5/5) N(75/10/10/5) N(40/30/25/5)

N(10/20/35/35) N(35/35/20/10) N(40/30/25/5) N(10/25/20/45) N(35/35/15/15)

N(35/30/30/5) N(15/30/25/30) N(35/30/15/20) N(20/35/40/5) N(20/30/25/25)

N(30/40/10/20) N(5/35/50/10) N(20/30/30/20) N(30/40/15/15) N(35/35/25/5)

N(20/35/20/25) N(20/40/15/25) N(45/25/10/20) N(20/35/20/25) N(20/30/25/25)

N(45/25/25/5) N(15/35/10/40) N(5/60/20/15) TCTCACACAGTAATAAACAGCCG

H3_12
(SEQ ID NO: 8)
AGGGTGCCTCTGCCCCA N(45/5/45/5) N(15/5/15/65) N(70/5/15/10) N(40/5/50/5)

N(5/5/5/85) N(5/85/5/5) N(45/5/45/5) N(85/5/5/5) N(75/5/15/5) N(10/30/55/5)

N(10/30/25/35) N(40/40/15/5) N(25/25/45/5) N(10/25/20/45) N(35/35/10/20)

N(40/40/15/5) N(20/20/35/25) N(40/30/15/15) N(10/40/45/5) N(20/25/30/25)

N(35/35/15/15) N(30/30/35/5) N(15/40/20/25) N(20/45/5/30) N(15/25/40/20)

N(20/30/25/25) N(20/40/15/25)N(15/25/40/20) N(20/35/20/25) N(25/40/15/20)

N(50/30/15/5) N(20/45/20/15) N(5/35/35/25) N(45/25/25/5) N(15/35/10/40)

N(5/65/15/15) TCTCACACAGTAATAAACAGCCG

H3_13
(SEQ ID NO: 9)
AGGGTGCCTCTGCCCCA N(45/10/40/5) N(15/5/15/65) N(75/5/15/5) N(35/5/55/5)

N(5/5/5/85) N(5/85/5/5) N(45/5/45/5) N(85/5/5/5) N(80/5/10/5) N(35/25/35/5)

N(10/30/25/35) N(40/45/10/5) N(15/25/55/5) N(10/25/10/55) N(35/35/10/20)

N(55/30/10/5) N(15/20/25/40) N(45/25/10/20) N(25/30/40/5) N(20/30/20/30)

N(30/35/15/20) N(15/25/55/5) N(15/35/20/30) N(25/45/10/20) N(10/45/40/5)

N(20/25/25/30) N(30/40/10/20)N(30/25/30/15) N(20/25/25/30) N(35/35/15/15)

N(25/30/30/15) N(20/30/20/30) N(25/35/20/20) N(40/30/25/5) N(20/45/20/15)

N(5/35/35/25) N(45/25/25/5) N(10/35/15/40) N(5/65/20/10)

TCTCACACAGTAATAAACAGCCG

H3_14
(SEQ ID NO: 10)
AGGGTGCCTCTGCCCCA N(50/5/40/5) N(20/5/15/60) N(60/10/25/5) N(35/5/55/5)

N(5/5/5/85) N(5/85/5/5) N(30/20/45/5) N(85/5/5/5) N(80/5/5/10) N(30/35/30/5)

N(10/35/20/35) N(40/40/15/5) N(50/25/20/5) N(10/25/10/55) N(40/30/10/20)

N(20/20/55/5) N(15/20/20/45) N(45/25/15/15) N(15/25/55/5) N(15/30/25/30)

N(35/30/15/20) N(40/30/25/5) N(15/25/25/35) N(35/35/10/20) N(20/30/40/10)

N(15/30/25/30) N(25/40/10/25)N(50/25/15/10) N(15/35/25/25) N(35/35/10/20)

N(15/25/45/15) N(15/30/25/30) N(35/35/10/20) N(15/30/40/15) N(20/30/20/30)

N(30/40/10/20) N(30/30/15/25) N(20/35/25/20) N(20/30/30/20) N(30/25/40/5)

N(10/30/15/45) N(5/70/15/10) TCTCACACAGTAATAAACAGCCG

H3_15
(SEQ ID NO: 11)
AGGGTGCCTCTGCCCCA N(30/5/45/20) N(45/5/5/45) N(45/35/5/15) N(45/5/45/5)

N(5/5/5/85) N(5/85/5/5) N(45/20/30/5) N(85/5/5/5) N(85/5/5/5) N(20/35/40/5)

TABLE 1-continued

N(5/40/25/30) N(35/50/10/5) N(15/5/75/5) N(10/10/20/60) N(50/30/10/10)

N(25/10/55/10) N(15/20/20/45) N(50/25/15/10) N(35/30/30/5) N(15/25/25/35)

N(50/20/15/15) N(35/5/35/25) N(10/30/30/30) N(35/35/10/20) N(20/40/35/5)

N(20/20/35/25) N(35/35/15/15)N(45/35/15/5) N(15/30/25/30) N(35/35/10/20)

N(35/35/25/5) N(20/30/20/30) N(30/35/10/25) N(30/25/40/5) N(15/30/20/35)

N(35/30/15/20) N(35/25/35/5) N(15/35/20/30) N(25/35/25/15) N(5/30/45/20)

N(20/35/20/25) N(15/30/30/25) N(45/25/25/5) N(15/35/10/40) N(5/70/15/10)

TCTCACACAGTAATAAACAGCCG

H3_16

(SEQ ID NO: 12)

AGGGTGCCTCTGCCCCA N(35/10/30/25) N(65/5/5/25) N(25/55/5/15)

N(45/5/45/5) N(5/5/5/85) N(5/85/5/5) N(35/30/30/5) N(85/5/5/5) N(75/5/5/15)

N(15/35/45/5) N(5/45/20/30) N(35/55/5/5) N(50/5/40/5) N(10/5/15/70)

N(60/20/10/10) N(65/5/25/5) N(10/10/25/55) N(55/15/15/15) N(30/5/60/5)

N(10/15/30/45) N(55/15/15/15) N(25/25/45/5) N(20/30/15/35) N(40/35/10/15)

N(40/20/30/10) N(20/30/25/25) N(35/30/10/25)N(45/30/15/10) N(15/35/25/25)

N(30/35/10/25) N(35/30/25/10) N(20/25/30/25) N(35/35/10/20) N(30/20/30/20)

N(20/35/20/25) N(30/40/10/20) N(45/10/25/20) N(20/25/20/35) N(30/35/15/20)

N(45/30/20/5) N(15/35/25/25) N(25/35/20/20) N(40/15/5/40) N(20/35/20/25)

N(15/30/30/25) N(30/30/35/5) N(15/30/15/40) N(5/75/15/5)

TCTCACACAGTAATAAACAGCCG

H3_17

(SEQ ID NO: 13)

AGGGTGCCTCTGCCCCA N(45/10/20/25) N(70/5/5/20) N(15/60/5/20)

N(40/5/50/5) N(5/5/5/85) N(5/85/5/5) N(25/20/50/5) N(85/5/5/5) N(80/5/5/10)

N(10/45/40/5) N(5/50/20/25) N(30/60/5/5) N(5/5/85/5) N(5/5/15/75) N(65/20/5/10)

N(45/5/45/5) N(10/10/20/60) N(55/10/20/15) N(45/5/45/5) N(15/15/20/50)

N(60/15/15/10) N(60/20/15/5) N(10/30/20/40) N(45/25/15/15) N(15/35/45/5)

N(15/15/35/35) N(40/30/15/15) N(30/25/40/5)N(20/30/25/25) N(30/35/10/25)

N(20/30/40/10) N(15/35/25/25) N(30/35/10/25) N(40/30/25/5) N(20/30/25/25)

N(40/35/10/15) N(35/20/40/5) N(20/25/20/35) N(40/35/10/15) N(35/20/40/5)

N(20/20/20/40) N(35/35/15/15) N(30/20/30/20) N(20/30/20/30) N(25/30/25/20)

N(35/35/25/5) N(25/35/20/20) N(5/35/40/20) N(20/30/45/5) N(15/30/10/45)

N(5/70/15/10) TCTCACACAGTAATAAACAGCCG

K3_9

(SEQ ID NO: 14)

GGACGAGGCTGATTATTACTGC N(5/85/5/5) N(85/5/5/5) N(5/5/85/5)

N(5/85/5/5) N(85/5/5/5) N(40/5/50/5) N(5/5/10/80) N(65/25/5/5) N(5/50/5/40)

N(30/5/25/40) N(60/10/20/10) N(5/40/10/45) N(80/5/10/5) N(30/15/50/5)

N(5/60/5/30) N(35/5/10/50) N(30/40/10/20) N(5/15/45/35) N(5/85/5/5) N(5/85/5/5)

N(5/5/85/5) N(5/40/5/50) N(30/10/25/35) N(5/35/50/10) N(85/5/5/5) N(5/85/5/5)

N(5/50/30/15) TTCGGCGGAGGGACCAAG

TABLE 1-continued

K3_10

(SEQ ID NO: 15)

GGACGAGGCTGATTATTACTGC N(5/85/5/5) N(85/5/5/5) N(5/5/85/5)

N(5/85/5/5) N(85/5/5/5) N(40/5/50/5) N(5/5/5/85) N(80/10/5/5) N(25/20/5/50)

N(35/5/40/20) N(45/5/45/5) N(5/30/15/50) N(75/10/10/5) N(40/5/50/5) N(5/45/5/45)

N(20/5/5/70) N(10/45/40/5) N(5/5/85/5) N(5/85/5/5) N(5/85/5/5) N(5/5/85/5)

N(5/85/5/5) N(5/65/15/15) N(5/5/85/5) N(15/5/10/70) N(20/5/30/45) N(5/30/50/15)

N(85/5/5/5) N(5/85/5/5) N(5/40/5/50)TTCGGCGGAGGGACCAAG

L3_9

(SEQ ID NO: 16)

GGACGAGGCTGATTATTACTGC N(5/85/5/5) N(80/5/5/10) N(5/5/85/5)

N(20/5/30/45) N(5/75/5/15) N(85/5/5/5) N(5/5/5/85) N(35/5/55/5) N(5/10/80/5)

N(5/10/80/5) N(80/10/5/5) N(5/60/5/30) N(65/5/25/5) N(15/10/70/5) N(5/65/5/25)

N(70/5/20/5) N(20/10/65/5) N(5/60/5/30) N(65/10/20/5) N(15/45/20/20)

N(5/40/10/45) N(15/5/50/30) N(10/15/25/50) N(5/20/70/5) N(10/5/80/5) N(5/5/5/85)

N(5/40/10/45)TTCGGCGGAGGGACCAAG

L3_10

(SEQ ID NO: 17)

GGACGAGGCTGATTATTACTGC N(45/5/10/40) N(15/15/60/10) N(10/50/5/35)

N(5/5/5/85) N(5/85/5/5) N(45/5/45/5) N(5/5/5/85) N(85/5/5/5) N(5/50/5/40)

N(25/5/65/5) N(45/45/5/5) N(5/45/5/45) N(55/35/5/5) N(10/10/75/5) N(5/40/5/50)

N(85/5/5/5) N(15/10/70/5) N(5/50/5/40) N(70/5/20/5) N(30/20/45/5) N(5/75/5/15)

N(70/15/10/5) N(25/45/15/15) N(5/35/5/55) N(5/15/35/45) N(15/5/30/50)

N(5/15/75/5) N(10/5/80/5) N(5/5/5/85) N(5/50/10/35) TTCGGCGGAGGGACCAAG

L3_11

(SEQ ID NO: 18)

GGACGAGGCTGATTATTACTGC N(10/55/25/10) N(65/20/10/5) N(5/10/80/5)

N(20/5/20/55) N(5/85/5/5) N(5/5/85/5) N(5/5/5/85) N(30/5/60/5) N(5/5/85/5)

N(5/5/85/5) N(85/5/5/5) N(5/45/5/45) N(75/5/15/5) N(20/10/65/5) N(5/60/5/30)

N(85/5/5/5) N(5/5/85/5) N(5/35/5/55) N(5/5/5/85) N(5/30/10/55) N(85/5/5/5)

N(75/5/15/5) N(45/20/30/5) N(5/20/5/70) N(5/30/50/15) N(25/25/35/15)

N(5/45/15/35) N(10/5/50/35) N(20/5/25/50) N(5/20/60/15) N(5/5/85/5) N(5/5/5/85)

N(70/5/20/5)TTCGGCGGAGGGACCAAG

*For the degenerated positions, the percentages of the 4 bases are given as N(A/C/G/T)

Other oligonucleotides use to construct the libraries were synthesized by MWG and have the following sequences:

T7.back CCGGATATAGTTCCTCCTTT; (SEQ ID NO: 19)

T7.for CTGCTAACCAGTAAGGCAAC; (SEQ ID NO: 20)

M13rev-49 GAGCGGATAACAATTTCACACAGG; (SEQ ID NO: 21)

M13uni-43 AGGGTTTTCCCAGTCACGACGTT; (SEQ ID NO: 22)

scFvCAT.rev AACGGTGGTATATCCAGTGA; (SEQ ID NO: 23)

scFvCAT2.rev CGGTGGTATATCCAGTGATTTTT; (SEQ ID NO: 24)

PliaisonH3 TGGGGCAGAGGCACCCT; (SEQ ID NO: 25)

PliaisonH3.back AGGGTGCCTCTGCCCCA; (SEQ ID NO: 26)

PliaisonL3 GCAGTAATAATCAGCCTCGTCC. (SEQ ID NO: 27)

Plasmids

Phagemid vector pCANTAB6 (McCafferty J et al., Appl Biochem Biotechnol 1994, 47:157-171) was used for N-terminal fusion of NcoI/NotI-scFv fragments to the minor coat protein pIII of filamentous phage M13. This phagemid is derived from pUC 119 and contains the following sequences in the following order: a lac promoter, the pelB leader sequence, NcoI and NotI sites for scFv cloning, a His6 and a c-myc tag recognized by the 9E 10 monoclonal antibody, an amber codon and the pIII gene sequence.

For cytoplasmic expression of the scFvs in *E. coli* we used plasmid pET23NN. This plasmid is derived from pET23d(+) (Novagen) and contains a T7 promoter, followed by a NcoI site containing the ATG initiator, a NotI site followed by a c-myc and a His6 tag.

Plasmid pscFv CAT is derived from pTrc99A and contains a tac promoter, followed by a NcoI site containing the ATG initiator of an out-of-frame scFv, a NotI site followed by the CAT gene. When a scFv is inserted within the NcoI-NotI sites, the scFv is expressed as a fusion with the CAT protein. The construction was done as follows: first, the unique BstEII site of pTrc99A (A13038) was removed by digestion followed by 5' overhang fill-in to form blunt ends, and ligation. The resulting plasmid was digested with NcoI and NotI, and the 4210bp fragment purified (fragment I). Second, the unique NcoI site of plasmid pACYC1 84 (X06403) located within the CAT gene was removed by site directed mutagenesis by changing the Thr172 codon from ACC to ACG. Then the CAT gene was amplified by PCR using CAT-NotI.for (TAAG<u>GCGGCCGC</u>AATGGAGAAAAAAATCACTG; SEQ ID NO: 28) and CAT-HindIII.back (ACTGCCTTAAA <u>AAGCTT</u>ACGCC; SEQ ID NO: 29). In the oligonucleotide sequences, the introduced restriction sites are underlined and the beginning and the end of the CAT gene are in bold-italic. The 660 by PCR fragment was digested by NotI and HindIII, and purified (fragment II). Third, a 750 by NcoI-NotI scFv 13E6 fragment (a grafted version of the scFv 13R4 containing the CDR loops of an anti-E6 monoclonal antibody. Philibert et al., to be published) was purified (fragment III). Fourth, the three fragments I, II and III were ligated to give plasmid pscFvCAT. Finally, an internal deletion of 165 by was introduced in the scFv by removing the fragment between the two PstI sites of the gene. The resulting plasmid, called pscFv-CAT, is Amp$^R$ and CAM$^S$ since the deletion of the PstI fragment resulted in a frameshift in the scFv.

Plasmid p513-EGFP is a derivative of pSG5 (Green, S., et al. *Nucleic Acids Res* 1988, 16:369) and harbors the EGFP coding region (Clontech, Inc.) under the control of the SV40 early promoter. The p513-scFv-EGFP constructs correspond to in frame fusions of the scFv's and the EGFP coding region with a linker of 10 residues.

The scFv coding regions were amplified with oligonucleotide primers

5'-ACTGATAAGCTTGCCACCATGGCCGAGGTGC (SEQ ID NO: 30)

and

5'-TTGATTACTAGTGAGTTTTTGTTCTGCGGCC (SEQ ID NO: 31)

and inserted into the HindIII-SpeI digested p51 3-EGFP vector.

Optimized Antibody Framework

To maximize the effectiveness of the scFv library, construction of the library began with the selection of a single optimized antibody framework for intrabody selection. Through molecular evolution, a human scFv called scFv13R4 was obtained, which is expressed at high levels in *E. coli* cytoplasm. This scFv is also expressed and has a soluble and active conformation in both yeast and mammalian cells. This scFv is very stable in vitro and can be renatured in presence of a reducing agent. In addition, analysis of its folding kinetics showed that it folds faster than the parent scFv and aggregates more slowly in vitro. The mutations isolated are mainly located in the VH domain and seem to be highly specific to this particular scFv since they cannot be transferred to a very homologous VH domain. The nucleotide and amino acid sequences of scFv13R4 are shown below.

Nucleotide and Amino Acid Sequence of scFv13R4 (from Nucleotides 1 to 819)

```
         ---------|---------|---------|---------|---------|---------|
    1    atggccgaggtgcagctggtggagtctggggaagcctggtcaagcctggggggtccctg    60
    1    M  A  E  V  Q  L  V  E  S  G  G  S  L  V  K  P  G  G  S  L    20

---------|---------|---------|---------|---------|---------|
   61    agactctcctgtgcagcctctggattcaccttcagtaactatagcatgaactgggtccgc   120
   21    R  L  S  C  A  A  S  G  F  T  F  S  N  Y  S  M  N  W  V  R    40

---------|---------|---------|---------|---------|---------|
  121    caggctccagggaaggggctggagtggatctcatccattagtggtagtagtagatacata   180
   41    Q  A  P  G  K  G  L  E  W  I  S  S  I  S  G  S  S  R  Y  I    60

---------|---------|---------|---------|---------|---------|
  181    tactacgcagacttcgtgaagggccgattcaccatctccagagacaacgccacgaactca   240
   61    Y  Y  A  D  F  V  K  G  R  F  T  I  S  R  D  N  A  T  N  S    80

---------|---------|---------|---------|---------|---------|
  241    ctgtacctgcaaatgaacagcctgagagccgaggacacggctgtttattactgtgtgaga   300
   81    L  Y  L  Q  M  N  S  L  R  A  E  D  T  A  V  Y  Y  C  V  R   100

---------|---------|---------|---------|---------|---------|
  301    tccagtattacgatttttggtggcggtatggacgtctggggcagaggcaccctggtcacc   360
  101    S  S  I  T  I  F  G  G  G  M  D  V  W  G  R  G  T  L  V  T   120

---------|---------|---------|---------|---------|---------|
  361    gtctcctcaggtggaggcggttcaggcggaggtggcagcggcggtggcggatcgcagtct   420
  121    V  S  S  G  G  G  G  S  G  G  G  G  S  G  G  G  G  S  Q  S   140

---------|---------|---------|---------|---------|---------|
  421    gtgctgactcagcctgcctccgtgtctgggtctcctggacagtcgatcaccatctcctgc   480
  141    V  L  T  Q  P  A  S  V  S  G  S  P  G  Q  S  I  T  I  S  C   160

---------|---------|---------|---------|---------|---------|
  481    gctggaaccagcagtgacgttggtggttataactatgtctcctggtaccaacaacaccca   540
  161    A  G  T  S  S  D  V  G  G  Y  N  Y  V  S  W  Y  Q  Q  H  P   180

---------|---------|---------|---------|---------|---------|
  541    ggcaaagcccccaaactcatgatttatgaggacagtaagcggccctcaggggtttctaat   600
  181    G  K  A  P  K  L  M  I  Y  E  D  S  K  R  P  S  G  V  S  N   200

---------|---------|---------|---------|---------|---------|
  601    cgcttctctggctccaagtctggcaacacggcctccctgacaatctctgggctccaggct   660
  201    R  F  S  G  S  K  S  G  N  T  A  S  L  T  I  S  G  L  Q  A   220

---------|---------|---------|---------|---------|---------|
  661    gaggacgaggctgattattactgcagctcatatacaaccaggagcactcgagttttcggc   720
  221    E  D  E  A  D  Y  Y  C  S  S  Y  T  T  R  S  T  R  V  F  G   240

---------|---------|---------|---------|---------|---------|
  721    ggagggaccaagctggccgtcctaggtgcggccgcagaacaaaaactcatctcagaagag   780
  241    G  G  T  K  L  A  V  L  G  A  A  A  E  Q  K  L  I  S  E  E   260

---------|---------|---------|---------
  781    gatctgaatggggccgcacatcaccatcatcaccattaa                          819  (SEQ ID NO: 32)
  261    D  L  N  G  A  A  H  H  H  H  H  H  *                           272  (SEQ ID NO: 33)
```

Methods

Database of CDR3 Sequences

Release 5 (August, 1992) of the Kabat database was used (Johnson, G., and Wu, T. T.: Kabat Database and its applications: 30 years after the first variability plot. *Nucleic Acids Res* 2000, 28:214-218). This dataset contained 44990 sequences. First, 4643 human VH sequences which were not a pseudogene and were not humanized were extracted. H3 sequences were then extracted from this dataset, first taking into account the nucleotide sequence when present, then the amino acid sequence. Finally, the 3469 complete H3 sequences that contained only the 20 regular amino acids were kept, among which 2703 were unique. The same procedure was followed for λ and κ light chains, respectively, resulting in 1044 and 1291 sequences from which 775 and 828 were unique.

CDR3 sequences from the IMGT/LIGM-DB database as it existed on 27 Nov. 2003 were also extracted (Giudicelli, V., et al. IMGT/LIGM-DB, the IMGT(R) comprehensive database of immunoglobulin and T cell receptor nucleotide sequences. *Nucleic Acids Res* 2006, 34:D781-784). Only the "productive/regular/human/cDNA+ RNA/rearranged" genes were considered. 5179H3, 1432 K3, and 1131 L3 sequences were obtained, of which 4323H3, 974 K3, and 812 L3 sequences were unique.

127 additional human antibody sequences were also collected from the Protein data bank (Berman, H. M., et al. The Protein Data Bank. *Nucleic Acids Res* 2000, 28:235-242.). For this we used the file of 510 sequences already compiled by Andrew Martin on Aug. 19, 2003 (Allcorn, L. C., and Martin, A. C. R. SACS—self-maintaining database of antibody crystal structure information. *Bioinformatics* 2002, 18:175-181).

Spiked Oligonucleotide Design

In biasing the representations of the amino acids, optimized mixtures of the nucleotides at each of the three codon positions were calculated as described previously (Wang, W., and Saven, J. G. Designing gene libraries from protein profiles for combinatorial protein experiments. *Nucleic Acids Res* 2002, 30:e120; Park, S., et al. Progress in the development and application of computational methods for probabilistic protein design. *Comput Chem Eng* 2005, 29:407-421.). Premature termination of protein sequences was limited by imposing an upper bound of 0.05 on the probability of realizing a stop codon. For the 34 positions which did not satisfactorily recover the desired probabilities of the amino acids, a second optimization was done with the same method, but with no constraint on the stop codon frequency. For oligonucleotide synthesis, the calculated frequencies were rounded in increments of 5% as follows: all the frequencies between 0% and 5% were rounded to 5%; other frequencies were rounded to the nearest 5%; if the resulting sum was higher than 100%, 5% was removed from the rounded amino acid frequency larger than 5% for which the difference between the rounded and the target frequency was maximal and the process iterated until the sum was 100%; if the sum was lower than 100%, 5% was added to the rounded frequency lower than 95%, for which the difference between the rounded and the target frequency was maximal and the process iterated until the sum was 100%.

Construction of VH and VL Libraries

Variable CDR3 sequences were introduced in scFv13R4 by PCR assembly using a hot-start proofreading polymerase (ProofStart, Qiagen) using as a template plasmid pAB1-scFv13R4p (Martineau, P., and Betton, J. M. In vitro folding and thermodynamic stability of an antibody fragment selected in vivo for high expression levels in *Escherichia coli* cytoplasm. *J Mol Biol* 1999, 292:921-929.) To introduce random H3 loops, the 5' of the gene with the random H3 sequence was obtained with oligonucleotides M13rev-49 and one of the 13 degenerate oligonucleotides, and the 3' was obtained with PliaisonH3 and M13uni-43 (both for 20 cycles at 55° C.). The two purified bands were thus assembled by PCR (30 cycles, 55° C.) using M13rev-49 and M13uni-43. The resulting PCR was purified using a commercial kit (Nucleospin, Macherey-Nagel), digested for 16 hours at 37° C. with NcoI and NotI enzymes, and then purified on a gel. The same procedure was followed to introduce random L3 and K3 loops except that the pairs of primers used were M13rev-49/PliaisonL3 for the 5' and one of the degenerate oligonucleotides encoding the L3/K3 loop (K3_n or L3_n) with M13uni-43 for the 3' part of the gene.

Each digested band was ligated for 16 hours at 16° C. with 1 µg of NcoI-NotI, digested, and purified pscFvΔCAT in 100 µl using 10 Weiss units of T4 DNA ligase. The ligation was heat inactivated and purified using a commercial kit (Nucleospin). The ligation was then electroporated in 300 µl of MC1061 competent cells (Sidhu, S. S., et al. Phage display for selection of novel binding peptides. *Methods Enzymol* 2000, 328:333-363) and plated on a 600 cm$^2$ square plate of LB containing 100 µg/ml of ampicillin, then incubated for 16 hours at 37° C. The 18 libraries (13 VH and 5 VL) were scrapped in 10 ml of LB with 10% glycerol, and 10$^9$ bacteria were immediately plated on a 600 cm$^2$ square plate of LB containing 100 µg/ml of ampicillin, 1 mM IPTG and 30 µg/ml of CAM, then incubated for 16 hours at 37° C. The 18 libraries were then scrapped in 10 ml of LB with 10% glycerol and frozen at –80° C. An aliquot was used to prepare DNA for the library assembly.

Library Assembly

The 13 VH libraries were amplified using primers M13rev-49/PliaisonH3.back using Pfu polymerase, and the 5 VL libraries were amplified using scFvCAT.rev/H3_Liaison (30 cycles, 55° C.). The 18 PCR bands were first purified, then carefully quantified on gel using ImageJ software. The 13 VH bands were pooled in amounts proportional to their frequency in human H3. This mix was called VHpool. The 2 VL κ bands were pooled in order to obtain 75% of 9 amino acid-length loops and 25% of 10 amino acid-length loops. The VL λ bands were pooled to obtain 30% of the 9, 30% of the 10, and 40% of the 11 amino acid-length loops. Finally, the κ and λ mixes were pooled in order to get 50% of each class in the final mix called VLpool.

VHpool and VLpool were assembled by PCR using Taq DNA polymerase and primers M13rev-49/scFvCAT2.rev in 500 µl (30 cycles, 55° C.). The PCR was successively digested with 20 units of NcoI and NotI for at least 6 h each, purified, and then quantified on gel. 50 µg of vector pCANTAB6 was successively digested with 80 units of NcoI and NotI for at least 6 h each, purified then quantified on gel. 5 µg of linearized pCANTAB6 was ligated with an equal molar amount of insert (0.84 µg) in 500 µl at 16° C. using 50 Weiss units of T4 DNA ligase. The ligation was heat inactivated and purified using a commercial kit (Nucleospin). The purified ligation was then electroporated in 10×300 µl of C-Max5αF' competent cells (Sidhu, S. S., et al. Phage display for selection of novel binding peptides. *Methods Enzymol* 2000, 328:333-363), and plated on ten 600 cm$^2$ square plate of LB containing 1% of glucose and 100 µg/m of ampicillin. After incubation for 16 h at 37° C., cells were scrapped in 2xYT containing 10% of glycerol and kept frozen at –80° C. in aliquots corresponding to twenty times the diversity.

Antigens

Aurora-A is an His-tagged protein and was produced in *E. coli*. GST:Syk was expressed in *E. coli*. (Dauvillier, S., et al. Intracellular single-chain variable fragments directed to the Src homology 2 domains of Syk partially inhibit Fc epsilon RI signaling in the RBL-2H3 cell line. *J Immunol* 2002, 169: 2274-2283). E6 protein from papillomavirus HPV16 was expressed in cyanobacterium Anabaena (Desplancq et al., to be published). Histones (a mix of H2a, H2b, H3 and H4) were purchased from Sigma (type II-AS. #H7755). Tubulin was purified from pig brain (Williams, R. C. J., and Lee, J. C. Preparation of tubulin from brain. *Methods Enzymol* 1982, 85 (Pt B):376-385).

Library Rescue and Selection

Library rescue was done essentially as previously described using a trypsin-sensitive helper phage (Kristensen, P., and Winter, G. Proteolytic selection for protein folding using filamentous bacteriophages. *Fold Des* 1998, 3:321-328). Briefly, an aliquot of the library corresponding to a 10 to 20-fold excess over the diversity (2-3×10$^{10}$ bacteria) was inoculated in 1000 ml of 2xYT containing 100 µg/ml ampicillin and 1% glucose and grown with shaking at 37° C. until OD$_{600nm}$ was 0.7. 200 ml (~3×10$^{10}$ cells) were infected with 5×10" helper phage KM13 (Kristensen, P., and Winter, G. Proteolytic selection for protein folding using filamentous bacteriophages. *Fold Des* 1998, 3:321-328) and incubated without shaking for 30 min at 37° C. Cells were pelleted, resuspended in 1000 ml of 2xYT containing 100 µg/ml ampicillin and 25 µg/ml kanamycin and incubated overnight with vigorous shaking at 30° C. The supernatant containing phages was precipitated twice by adding $\frac{1}{5}^{th}$ of the volume of PEG-8000 20%, NaCl 2.5 M, and resuspended in PBS supplemented with 15% of glycerol. Aliquots containing 10$^{11}$-10$^{12}$ phages were stored at –80° C.

To select for binders, 100 µl of purified antigens were coated in a Nunc Maxisorp 96-well plate. For the first round, an antigen concentration of 10-100 µg/ml was used. For subsequent rounds, an antigen concentration of 1-10 µg/ml was used. The plate was washed 3 times with PBS containing 0.1% of Tween20 (PBST) and saturated for 2 hours at room temperature with PBS containing 2% non-fat milk (MBPS). 10$^{11}$-10$^{12}$ phages were added per well in 2% MPBS and incubated for 2 hours at room temperature. The plate was washed 20 times (first round) or 40 times ($2^{nd}$ and $3^{rd}$ rounds) with PBST, and then washed 3 times with PBS. Excess PBS was removed, and the phages were eluted by adding 100 µl of 100 mM triethylamine for 10 minutes at room temperature. The eluted phage suspension was neutralized with 50 µl of 1 M Tris-HCl pH 7.4, then digested 15 minutes at room temperature with trypsin by adding 1.5 µl of 0.1 M $CaCl_2$ and 15 µl of 10 mg/ml TPCK-treated trypsin (Sigma). 1 ml of a 37° C. exponentially growing Cmax5αF' strain in 2xYT was infected with 40 µl of trypsin-treated phages, incubated 30 min at 37° C. without shaking, then plated on a 15 cm round Petri dish (LB, 100 µg/ml ampicillin, 1% glucose). After overnight incubation at 37° C., bacteria were recovered from the plate and used to prepare a new stock of phages using KM13 helper phage. $10^{11}$-$10^{12}$ phages of this stock were used for the next round of selection.

Periplasmic and Cytoplasmic Screening

For periplasmic screening, phages from round 3 were used to infect the non-suppressive strain HB2151. Individual clones were tested for scFv expression by ELISA on antigen-coated 96-well microtiter plates as described (Harrison, J. L., et al. Screening of phage antibody libraries. *Methods Enzymol* 1996, 267:83-109.) For cytoplasmic screening, plasmid was prepared from the pool of bacteria of the $2^{nd}$ or $3^{rd}$ selection round, digested with NcoI and NotI enzymes, and the 750 by band was cloned in NcoI-NotI digested and dephosphorylated plasmid pET23NN. Ligation was transformed in C-Max5αF', and the cells were plated on LB with 100 µg/ml ampicillin and incubated for 16 hours at 37° C. Cells were scrapped, and the plasmid DNA was prepared and used to transform chemically competent BL21(DE3) pLysS. Individual clones were grown in a 96-well microtiter plate containing 100 µl of 2xYT, 100 µg/ml of ampicillin with vigorous shaking at 37° C. until $OD_{600nm}$ reached 0.6. IPTG was added to 0.4 mM final and the microtiter plate was incubated for 16 hours at 24-30° C. with vigorous shaking in a humidified atmosphere. After centrifugation, cells were resuspended in 100 µl of 50 mM Tris-HCl pH7.5, 5 mM EDTA, freeze/thawed, and incubated 1 hour on ice. $MgCl_2$ was added up to 10 mM and the DNA was digested with 10 µg/ml of DNAseI. 5-20 p. 1 were used in an ELISA on an antigen-coated 96-well microtiter plate (Nunc Maxisorp). Revelation was done using 9E10 monoclonal antibody followed by an HRP conjugated anti-mouse IgG antibody.

Purification of scFv scFvs cloned in plasmid pET23NN were purified from the cytoplasm of BL21(DE3) pLysS and purified on a Ni-NTA column as described for the parental scFv13R4 (Martineau, P., et al. Expression of an antibody fragment at high levels in the bacterial cytoplasm. *J Mol Biol* 1998, 280:117-127.).

Cell Transfection and Immunofluorescence

HeLa cells were maintained in Dulbecco's modified Eagle's tissue culture medium (DMEM; Invitrogen) supplemented with L-glutamine (2 mM), penicillin (100 Mimi), streptomycin (25 µg/ml) and 10% heat-inactivated fetal calf serum at 37° C. in a humidified 5% $CO_2$ atmosphere. Transient transfection was carried out with the TransFectin lipid reagent (Bio-Rad, Hercules, Calif., USA) according to the manufacturer's instructions. Cells were seeded on coverslips in 6-well plates at $2.5 \times 10^5$ cells/well the day before transfection. 1 µg DNA and 2 µl of reagent diluted in 100 µl of DMEM were mixed and left at room temperature for 20 minutes. Cells were grown at 37° C. for 24 hours after addition of the mixture. The expressed GFP-tagged proteins were visualized after fixation of the transfected cells with 4% paraformaldehyde in PBS for 45 minutes at room temperature. After extensive washing with PBS, cells were dried and mounted with Fluoromount-G (SouthernBiotech, Birmingham, UK). The processed cells were examined with a Zeiss Axioplan fluorescence microscope equipped with an Olympus DP50 camera. Images were collected with a Zeiss 40× plan-neofluar objective and processed using Adobe Photoshop 5.5. For FIG. 8, HeLa were transfected with anti-histones clone 5 fused to the dsRed-monomer GFP, fixed as above and permeabilized with Triton x-100 (0.2%, 5 min). The microtubule network was revealed with the 2F12C scFv (Table 3) at 3 µg/ml using the 9E10 anti-myc and an Alexa Fluor 488 anti-mouse IgG antibody. Cells were observed by confocal microscopy (×63).

Results

Step 1: Selection of Antibody Framework

In order to maximize the effectiveness of the scFv library, construction of the library began with the selection of a single optimized antibody framework for intrabody selection. Through molecular evolution, a human scFv called scFv13R4 was obtained, which is expressed at high levels in *E. coli* cytoplasm. This scFv is also expressed and has a soluble and active conformation in both yeast and mammalian cells. This scFv is very stable in vitro and can be renatured in presence of a reducing agent. In addition, analysis of its folding kinetics showed that it folds faster than the parent scFv and aggregates more slowly in vitro. The mutations isolated are mainly located in the VH domain and seem to be highly specific to this particular scFv since they cannot be transferred to a very homologous VH domain. The nucleotide and amino acid sequences of scFv13R4 are shown below.

Step 2: Introduction of Diversity into CDR3Sequences a) Database of Human CDR3 Sequences Human CDR3 sequences were compiled from three main sources: the Kabat database (Johnson, G. and Wu, T. T. Kabat Database and its applications: 30 years after the first variability plot. *Nucleic Acids Res* 2000, 28:214-218), the IMGT database (Giudicelli, V., et al. IMGT/LIGM-DB, the IMGT (R) comprehensive database of immunoglobulin and T cell receptor nucleotide sequences. Nucleic Acids Res 2006, 34:D781-784), and the RCSB PDB (Berman, H. M., et al. The Protein Data Bank. Nucleic Acids Res 2000, 28:235-242). After removing the duplicates, the database contained 5179H3, 1432 K3, and 1131 L3 CDR3 unique sequences. It can be noted that most of the 1-13 sequences were unique since, for instance, in the Kabat database, 2368H3 sequences (88%) were found only once among the 2703 complete 113 sequences. The result was comparable in the case of L3 and K3 since, respectively, 87% and 82% of the sequences were unique in the Kabat database. This underlines the very high variability of the human CDR3 sequences.

This variability, however, is not evenly distributed in the loop, and the frequency of each amino acid varies from one position to another and for each loop length. In addition, the amino acid distribution depends on the origin of the antibody sequence. This bias can be due to a structural constraint as for instance in the case of the antepenultimate residue which is frequently an aspartate (D101 using Kabat numbering scheme) and plays an important role in the switch between the extended and the kinked conformation of the H3. In other cases, this bias may only be due to the limited number of sequences available for the D and J segments, and amino acids other than those found in natural antibodies may be tolerated.

For the construction of the library it was decided to make CDR3s that mimic the natural distribution for two main reasons: i) one goal was to generate scFvs that would be as human as possible for possible use in human therapy; and ii) maintaining the natural amino acid distribution will more likely result in functional antibodies.

CDR3 sequences from the database were aligned by length, and the frequency for each of the 20 possible amino acids at each position and for each loop length were calculated. In the case of the light chain CDR3, sequences were analyzed independently for each class. In the case of the H3 sequences, this resulted in 35 tables, one for each 1-13 length between 1 and 34 amino acids. For a loop of length n, this table contained 20n frequencies.

b) Oligonucleotide Design for Encoding CDR3 Loops

Eighteen oligonucleotides were designed to follow the amino acid distribution found in the compiled CDR3 database. One-hundred-ninety-two optimized mixes of the four nucleotides at each position of the codon were used, to match as well as possible with the desired amino acid distribution. The main advantage of this approach is that it only requires classical oligonucleotide synthesis resulting in better oligonucleotide quality. Due to the restrictions of the genetic code, however, it is not possible to follow precisely an arbitrary amino acid distribution. In addition, if the library does not strictly follow the natural amino acid distribution, this may introduce interesting non-natural diversity in the CDR3 loops.

Optimized mixes for the 249 variable positions were first calculated to match the distribution with a minimal frequency of stop codons, then 34 positions which were too distant from the target distribution were further optimized by relaxing this last constraint. Due to the constraint of the genetic code, some positions were not perfectly optimized. For instance, at position 3, alanine and glycine were under-represented in our mix and it was necessary to introduce a substantial amount of some non-naturally found amino acids like cysteine in order to match other amino acid frequencies. There was, however, a good overall agreement between the database and the oligonucleotide-encoded frequencies since the most frequently found amino acids were represented at the highest rates in the library and the rare amino acids were usually present at a low frequency. The sequences of the 18 degenerate oligonucleotides used to construct the CDR3 loops are provided above.

c) Construction of CDR3 Loop Libraries for VH and VL Chains

Independent libraries for each CDR3 loop length were constructed. This was done independently for each of the heavy and the two classes of light chains. For each library, random CDR3 loops were introduced by PCR and the resulting library was then cloned back in the scFv 13R4 gene, which was fused to the CAT gene in vector pscFvCAT. This resulted in libraries of scFv 13R4 clones with one and only one randomized CDR3 loop.

The 5 amino acid long H3 loop library was constructed first. Forty-three randomly chosen clones were sequenced. Some positions diverged from the expected values of frequencies for the 20 amino acids, but on average, the distribution of amino acids in the library matched the expected distribution. This showed that the quality of the oligonucleotides was good and that the resulting library followed the natural distribution of the amino acid in human H3 loops.

TABLE 2

Diversity of the CDR3 libraries

| | Initial diversity[a] | CAM phenotype[b] | | | final diversity[c] |
|---|---|---|---|---|---|
| | | ++ | + | − | |
| H3-5 | 1.4e8 | 15/20 | 3/20 | 2/20 | 1.1e8 |
| H3-6 | 2.7e7 | 20/20 | 0/20 | 0/20 | 2.7e7 |
| H3-7 | 9.2e7 | 16/20 | 3/20 | 1/20 | 7.4e7 |

TABLE 2-continued

Diversity of the CDR3 libraries

| | Initial diversity[a] | CAM phenotype[b] | | | final diversity[c] |
|---|---|---|---|---|---|
| | | ++ | + | − | |
| H3-8 | 5.0e6 | 14/20 | 4/20 | 2/20 | 3.5e6 |
| H3-9 | 2.4e8 | 16/20 | 1/20 | 3/20 | 1.9e8 |
| H3-10 | 1.0e7 | 10/20 | 6/20 | 4/20 | 5.0e6 |
| H3-11 | 2.2e7 | 9/12 | 1/12 | 2/12 | 1.7e7 |
| H3-12 | 1.0e7 | 15/20 | 2/20 | 3/20 | 7.5e6 |
| H3-13 | 2.3e7 | 8/12 | 3/12 | 1/12 | 1.5e7 |
| H3-14 | 1.0e7 | 12/20 | 4/20 | 4/20 | 6.0e6 |
| H3-15 | 2.1e7 | 8/12 | 3/12 | 1/12 | 1.4e7 |
| H3-16 | 1.0e7 | 12/20 | 2/20 | 6/20 | 6.0e6 |
| H3-17 | 1.1e7 | 12/20 | 4/20 | 4/20 | 6.6e6 |
| K3-9 | 3.6e6 | 11/16 | 1/16 | 4/16 | 2.5e6 |
| K3-10 | 4.4e6 | 10/16 | 1/16 | 5/16 | 2.8e6 |
| L3-9 | 1.7e7 | 11/20 | 6/20 | 3/20 | 9.4e6 |
| L3-10 | 1.5e7 | 10/20 | 9/20 | 1/20 | 7.5e6 |
| L3-11 | 1.8e7 | 15/20 | 3/20 | 2/20 | 1.4e7 |

[a]Initial diversity of the library cloned as fusion with CAT and selected on ampicillin. This is the number of clones obtained after transformation.
[b]Between 12 and 20 clones from the transformation were checked on CAM plates. Plates were incubated for 16 h at 37° C. and colony size estimated. Columns ++, + and − give, respectively, the fraction of clones that grew normally, gave tiny colonies, and did not grow at all.
[c]Diversity of the libraries selected on CAM. The diversity is estimated from column "Initial Diversity" and "CAM phenotype" by assuming that the final diversity is close to (Initial Diversity) × (CAM phenotype ++). The real diversity may be a higher since some of the clones noted + in column "CAM phenotype" may be present in low abundance.

Step 3: Removal of Non-Expressed Sequences

As expected, not all of the clones formed from the construction of the VH and VL libraries were functional for three main reasons: i) oligonucleotides used to introduce diversity may contain stop codons; ii) stop codons or frameshifts may be introduced by the PCR and the cloning steps; or iii) the scFvs are poorly expressed in the cytoplasm. To remove these non-functional scFv clones, expressed clones were selected by fusing the scFv gene and the chloramphenicol acetyl transferase (CAT) enzyme using the method of Maxwell K L et al. (A simple in vivo assay for increased protein solubility, Protein Sci 1999; 8:1908-1911) as described below.

Creation of scFV-CAT Fusion Proteins

Briefly, the scFv libraries were independently cloned between the NcoI and NoI sites of vector pscFvCAT under the control of the tac promoter and in frame with a downstream CAT gene. The scFv-CAT fusion protein was thus expressed in the cytoplasm. If a scFv was not properly expressed because of the inclusion of a stop codon or frameshift mutation, or if it was unable to fold in the cytoplasm, the resulting scFv-CAT protein would be either not expressed or not active, resulting in a chloramphenicol sensitive ($CAM^S$) phenotype. On the other hand, if the scFv was properly expressed, the resulting scFv-CAT protein would be well expressed in the cytoplasm, and the bacterium would be chloramphenicol resistant ($CAM^R$). By adjusting the chloramphenicol (CAM) concentration, one can even select for expression of different solubility levels of the scFv-CAT protein.

Different CAM concentrations were tested for this selection step ranging from 15 to 200 µg/ml. At the highest concentration of CAM, the library was enriched in well-expressed scFvs, but also in clones containing recombined plasmids harboring partial or complete deletions of the scFv gene. Next, the libraries were plated on a medium CAM concentration (30 µg/ml). This concentration was high enough to remove all the non-expressed or strongly aggregating scFvs, but did not result in a detectable amount of plasmids harboring scFv deletion.

To estimate the final size of the libraries, at least 12 clones were isolated from each initial library, which was selected on ampicillin and on CAM to determine the fraction of $CAM^R$ clones. Some clones grew quickly and formed colonies on ampicillin/CAM/IPTG plates (Table 2, column ++), some grew slowly (column +), and some did not grow at all (column −). The size of the libraries of expressed scFv (selected on Amp+CAM+IPTG) was thus estimated as the product of the original library size (selected on ampicillin) by the frequency of the $CAM^R$ clones. The sizes of the 18 libraries are given in the last column of Table 2 and ranged from $2.5 \times 10^6$ to $1.9 \times 10^8$.

Step 4: Assembly of CAM-Selected Library

The final library was assembled by recombining the 13 CAM-selected VH libraries with the 5 CAM-selected VL libraries. The theoretical possible diversity is about $10^{15}$ (~13 VH×$10^7$×5 VL×$10^6$). This is much larger than a library that could be obtained by electroporation. It is thus very unlikely to obtain twice the same clone in the final library.

The 13 VH and 5 VL libraries were amplified by PCR with an overlapping sequence of 17 nucleotides, then purified and quantified on agarose gel. The VH and VL purified fragments were then pooled in amounts proportional to the natural distribution of the CDR3 loop lengths in human antibodies (FIG. 3a). Finally, the VH and VL mixes were assembled by PCR, digested and cloned in a vector suitable for phage display. The library was electroporated in strain Cmax5αF', resulting in a library of $1.5 \times 10^9$ clones containing a scFv insert, as checked by PCR on 100 randomly picked colonies. The 18 CAM-selected libraries were assembled in amounts proportional to the natural distribution of CDR3 loops lengths in human antibodies to form a final library of more than a billion clones.

One hundred and eighteen clones were sequenced to determine loop lengths and sequences. Almost all loop lengths were found in the library. 11 and 16 amino acid long loops were also under-represented in the library. This is presumably due to the poor quality of these oligonucleotides as shown by their profile on an Agilent Bioanalizer. Loop lengths ranging from 7 to 12 were over-represented in the library but only by a two-fold factor. The loop lengths between 8 and 17 amino acids, which are the most frequently found in human antibodies, were all present in the library. The number of sequenced clones was too small to analyze the frequency of the amino acids found in the CDR3 loops. Except for some contamination with the original scFv 13R4 sequence, no CDR3 sequence was found twice in the library.

Expression of scFvs in the Cell

Because of the novel use of the CAM selection step, the VH and VL libraries were independently optimized for expression in the cell. Because of this optimization of the VH and VL libraries the result should be only expressed scFv proteins. Furthermore, since only the CDR3 loops are modified between the original scFv 13R4 antibody framework and the resulting scFv libraries, most of the interface residues between the two domains are conserved between clones. It is thus likely that any VH will assemble correctly with any VL and that the expression level of the resulting scFv will be close to that of both clones from the VH and VL libraries selected on CAM. In other words, if a VH, with a modified H3 loop, is well expressed when fused to the VL13R4, it will be also well expressed when coupled with a VL with a modified CDR3 loop and selected as a fusion with the VH1 3R4. This hypothesis was tested by picking random clones from the final library and expressing them in E. coli cytoplasm and in mammalian cytosol.

Figure 3:
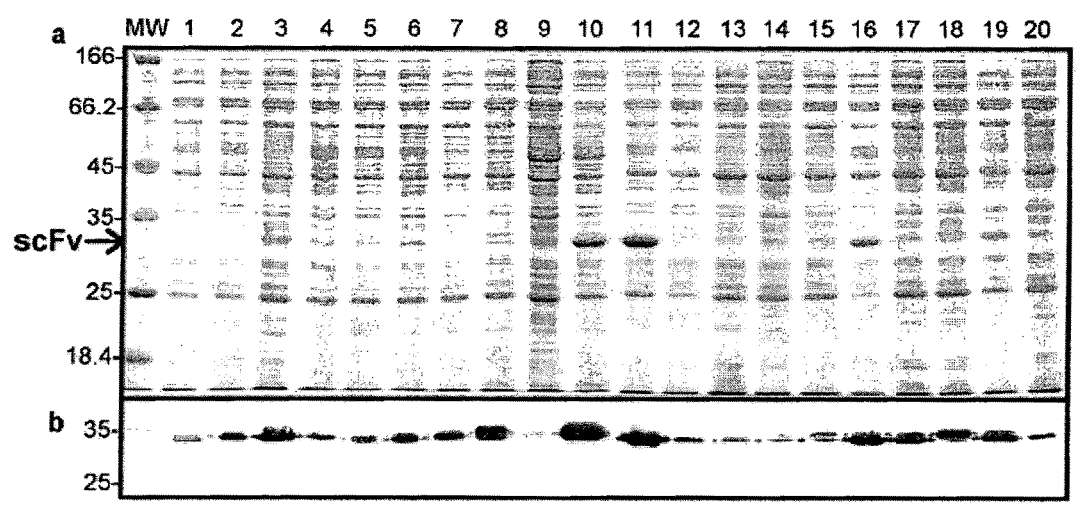
FIG. 3. Western blot analysis of twenty clones from the library that were cloned in a cytoplasmic expression vector and expressed in $E.\ coli$ under the control of the T7 promoter. Twenty clones from the library were cloned in a cytoplasmic expression vector and expressed in $E.\ coli$ under the control of the T7 promoter. Soluble extracts were prepared, separated by SDS-PAGE, and analyzed by Coomassie staining (a) or Western-blot (b) using 9E10 and an alkaline phosphatase conjugated anti-mouse IgG antibody (substrate BCIP/NBT). Each lane corresponded to $2 \times 10^7$ ($2 \times 10$ to the $7^{th}$) cells. The arrow on the left indicates the position of the scFv.

DNA was prepared from the final library and the scFv genes cloned in a plasmid for cytoplasmic expression under the control of the strong T7 promoter. It must be noted that the very high expression levels obtained under such a strong promoter favor aggregation over soluble expression because of the high kinetics order of the aggregation process. The stringency of this test is thus high and it could be possible to increase the soluble versus insoluble ratio by using a weaker promoter. Twenty clones were tested in E. coli and 19 of them showed at least some soluble expression in the cytoplasm (FIG. 3). One-fourth of the clones (5/20; clones 3, 10, 11, 16, 19) were expressed at very high levels since the scFvs were clearly visible on a Coomassie stained gel. To obtain a more global view of the soluble expression levels in E. coli, the library was cloned in front of the GFPuv gene under the control of the T7 promoter. If the scFv is soluble and expressed in the cytoplasm, this should result in green fluorescent protein (GFP) activity that can be directly monitored on an UV transilluminator. About 1000 clones were tested for the presence of detectable GFP activity and approximately 60% exhibited a $GFP^+$ phenotype, which again indicated that most of the scFv clones from the final library were correctly expressed in E. coli cytoplasm. These two tests demonstrated that the novel method of constructing an scFv library as described above was very successful in generating cytoplasmically expressed scFvs in E. coli.

Figure 4:
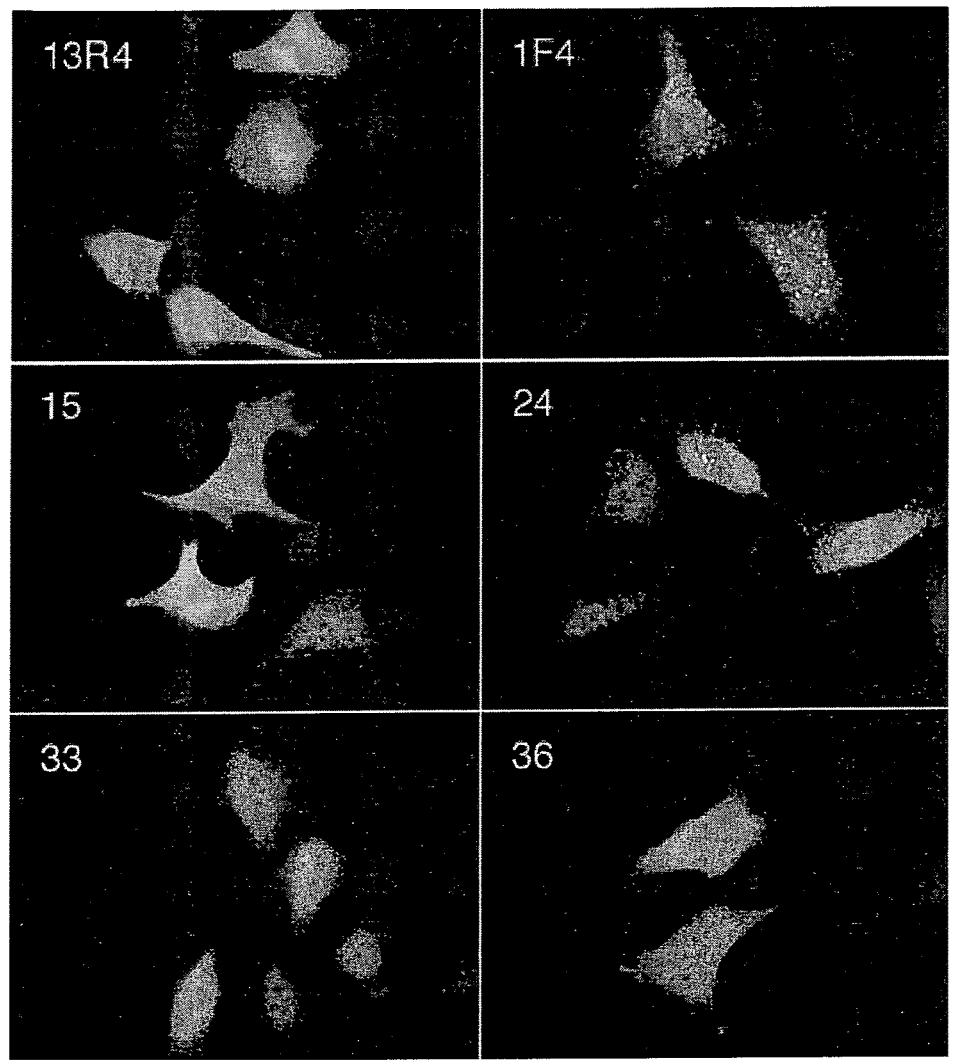
FIG. 4. Selected fluorescent micrographs of expression of randomly picked scFvs in HeLa cells. Cells were transfected with scFv-EGFP constructs as indicated. 13R4 and 1F4 represent the positive and negative controls, respectively. At 24 h post-transfection, cells were fixed and visualized under a fluorescent microscope with the fluorescein isothiocyanate filter set. The micrographs represent typical fields containing a similar number of cells in each case. Magnification: ×400.
Figure 5:
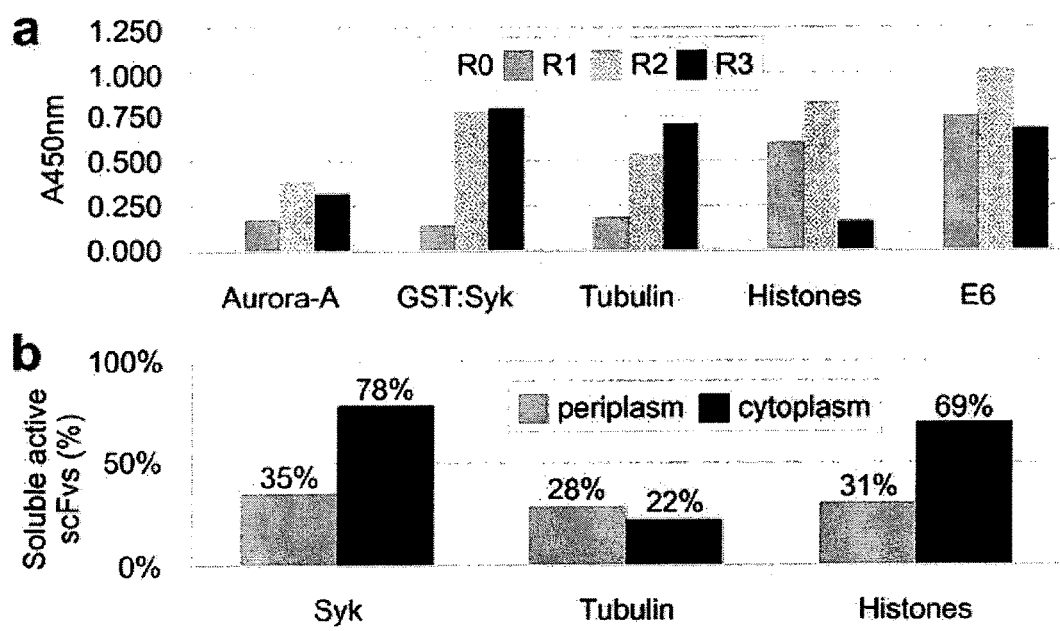
FIG. 5. Selection of binders against five purified proteins. (a) $2.5 \times 10^{10}$ phages from each round of selection were tested by ELISA against their respective antigen and revealed using an anti-M13 HRP conjugated monoclonal antibody (Pharmacia). R0 is the non selected library and Rn the stock obtained after the $n^{th}$ round of selection. Specificity was tested on BSA for the $3^{rd}$ rounds of selection (A450 nm ~0.1-0.3). (b) Monoclonal phages from each round of selection against GST:Syk protein were tested by ELISA as in (a). Percentage of soluble active scFvs (Absorbance>0.1) selected after three rounds against the indicated protein and expressed either in the periplasm (gray) or in the cytoplasm (black).

Next, the expression of the library in mammalian cells was tested. Fifteen scFvs were cloned in a mammalian expression vector as fusions with the EGFP gene and under the control of the SV40 early promoter, then transfected in HeLa cells. Typical results are shown in FIG. 4. Three clones were expressed at a high soluble level, comparable to that of the parental scFv13R4 (clone 15), 10 scFvs were found to be mainly soluble but some aggregated material was still present in the cell (clones 33 and 36), and 2 clones accumulated essentially as cytoplasmic aggregates (clone 24), as observed with the hybridoma-derived anti-oncoprotein E6 scFv 1F4 (FIG. 4). In conclusion, thirteen out of the fifteen scFvs tested were expressed as soluble proteins that could be easily detected in the cytoplasm and in the nucleus of the transfected cells.

Together, these results showed that more than 85% of the clones from the final library expressed soluble scFv in E. coli (16/20) and mammalian cytoplasm (13/15), while about 20% of them expressed scFv at a very high level (5/20 in E. coli and 3/15 in eukaryotic cells). Overall, most of the clones were well expressed under the reducing conditions of the bacterial and eukaryotic cytoplasm. This is a great improvement over results previously obtained with non-optimized scFv libraries.

Selection of Binders

As shown above, the library contains a very high proportion of expressed clones. The next step was selecting antibodies from the library against particular proteins. Thus, the phage display library was used to select for binders against five different antigens using purified proteins adsorbed on microtiter plates. Three rounds of selection were performed, and the eluted phages were tested by ELISA against the immobilized antigens. In all the cases a positive signal was obtained after a single round of selection. This signal increased strongly after two rounds and did not increase further during the third round of selection. This very fast selection process was presumably due both to the focused library itself, which contains only expressed scFvs resulting in a low background, and to the use of a trypsin sensitive helper phage that further decreased the background level.

Figure 7:
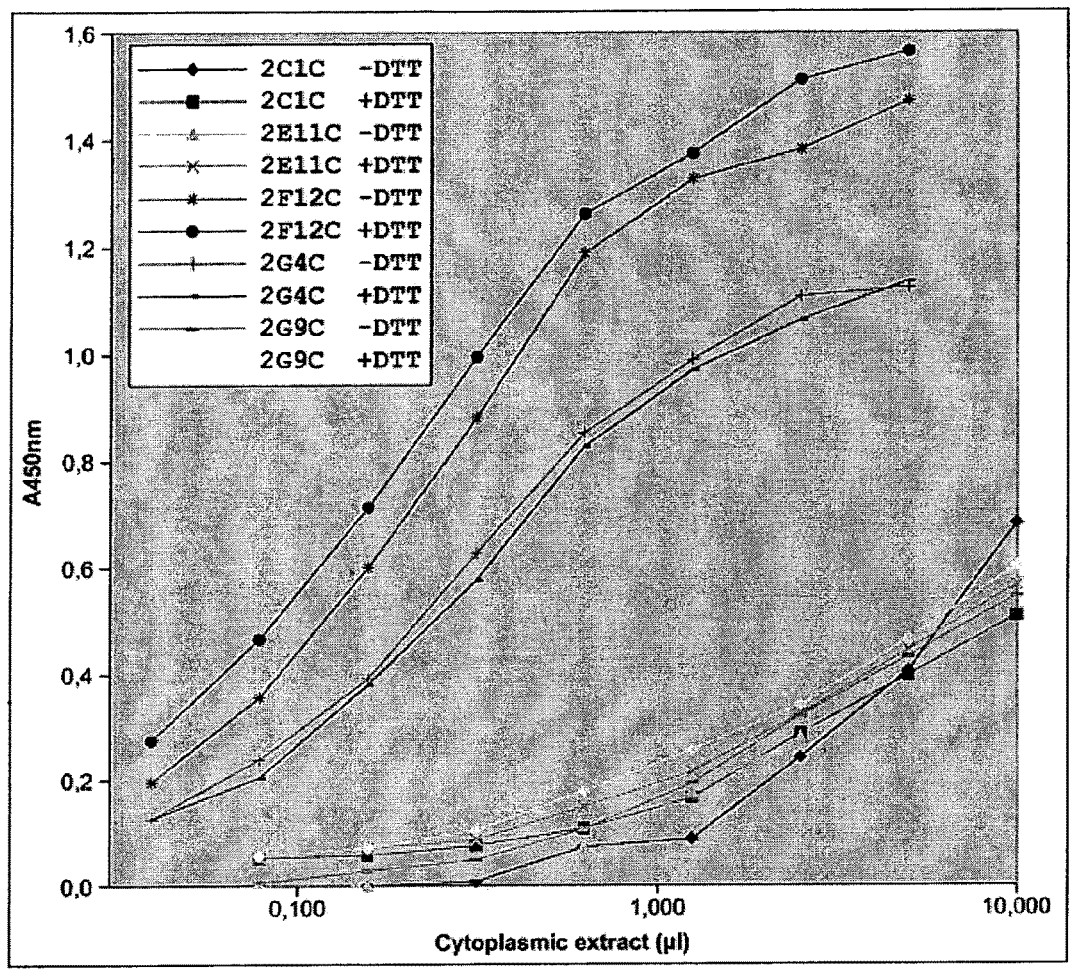
FIG. 7. Graphical representation of the expression of the activity of selected scFvs under reducing conditions. Extracts of cells expressing the scFvs in the cytoplasm were prepared as in FIG. 3 in presence or absence of 10 mM DTT. ELISA was performed in presence or absence of DTT, accordingly. x-axis: amount of extract per well. y-axis: ELISA signal at 450 nm.

To characterize the selection process, 60 clones were selected from the three selection rounds against GST:Syk fusion. These clones were used to prepare monoclonal phages, which were then tested for binding to the antigen by ELISA. FIG. 7 shows the distribution of the ELISA values obtained for each selection round. The distribution was normal with a strong homogeneity of the signal in each round of selection since more than half of the clones showed an ELISA signal within 0.1 of the peak value. During the selection process the peak signal increased from 0.4-0.5 after a single round to 0.9 after round 2 and 1.0 after round 3, in good correlation with the results obtained with the polyclonal phages. Moreover, after a single round of selection nearly 100% of the clones already recognized the antigen. This showed that using the optimized library in combination with a trypsin-sensitive helper phage results in almost a total absence of background during the selection process.

Next tested was whether the library contained clones expressing soluble scFvs in the periplasm. The non-suppressive HB2151 strain was infected with the phages eluted after the third round of selection against tubulin, GST:Syk and the core histones. Periplasmic extracts were prepared and tested for binding activity by ELISA. In the three cases, 12-20% of the clones gave a strong signal with absorbance values higher than 0.5 (10 times the background), and about 30% were clearly positive with an absorbance value higher than 0.1 (twice the background). These results compared favorably with those reported with other scFv libraries, underlining again the high proportion of well-expressed clones present in the library. In addition, this showed that the CAM-selection approach selected efficiently for constructs without stop codons present in the oligonucleotides. This is indeed of premium importance to isolate soluble scFvs from phage-displayed libraries since amber stop codons in CDRs are frequently selected during panning of synthetic and semi-synthetic libraries.

In both the previous characterizations, the scFvs were expressed under oxidizing conditions in *E. coli* periplasm, either as scFv-pIII fusion or as soluble protein. In addition, panning was done on phage, again under oxidizing conditions. To test whether the scFvs were indeed also expressed in the cytoplasm, the same pool of clones (Round 3) was subcloned in a cytoplasmic expression vector under the control of the strong T7 promoter. For each antigen, ninety-five clones were tested by ELISA for binding to their respective antigen. In each case, the number of positive clones was comparable or even better than in the periplasmic screen. For instance, in the case of GST:Syk, 80% of the tested clones were positive after three rounds of selection. This demonstrated that the periplasmic selection step did not decrease the proportion of soluble scFvs in the cytoplasm. Furthermore, when using the optimized library as described above it is not necessary to directly select within the cytoplasm to avoid introducing a bias during the selection.

Individual clones from the 2nd and the 3rd round of selection against tubulin were sequenced. Sequences are shown in Table 3.

TABLE 3

Sequences of some anti-tubulin scFvs

| Name | VH CDR3 Sequence | length | VL CDR3 Sequence | length | frequency[a] | yield[b] | WB[c] | IF[d] |
|---|---|---|---|---|---|---|---|---|
| Round 2 | | | | | | | | |
| C12C | SSITIFGGGMDV (SEQ ID NO: 34) | 12 | HSREVHRTF (SEQ ID NO: 35) | 9 | 1/5 | 19 | | |
| E12C | SGGNTFDY (SEQ ID NO: 36) | 8 | QQYYRKPWT (SEQ ID NO: 37) | 9 | 1/5 | 53 | | |
| F1C | GNADGGENWELFDK (SEQ ID NO: 38) | 14 | QLYQNTLWT (SEQ ID NO: 39) | 9 | 2/5 | 52 | | |
| H6C | SSITIFGGGMDV (SEQ ID NO: 40) | 12 | QQNWTSPLS (SEQ ID NO: 41) | 9 | 1/5 | nd | | |
| Round 3 | | | | | | | | |
| 2C1C | RGRDY (SEQ ID NO: 42) | 5 | QQYNTSPFS (SEQ ID NO: 43) | 9 | 1/6 | 8.6 | + | − |
| 2E11C | GRNVLNY (SEQ ID NO: 44) | 7 | QQNSSSPRFT (SEQ ID NO: 45) | 10 | 2/6 | 8.7 | + | − |
| 2F12C | GRRALGN (SEQ ID NO: 46) | 7 | QQYNTSPFS (SEQ ID NO: 47) | 9 | 1/6 | 45 | + | + |
| 2G4C | GRRALGN (SEQ ID NO: 48) | 7 | LTWSMRSAI (SEQ ID NO: 49) | 9 | 1/6 | 15 | + | + |
| 2G9C | GRRALGN (SEQ ID NO: 50) | 7 | LTTENSVYRLV (SEQ ID NO: 51) | 11 | 1/6 | 50 | + | − |

Figure 8:
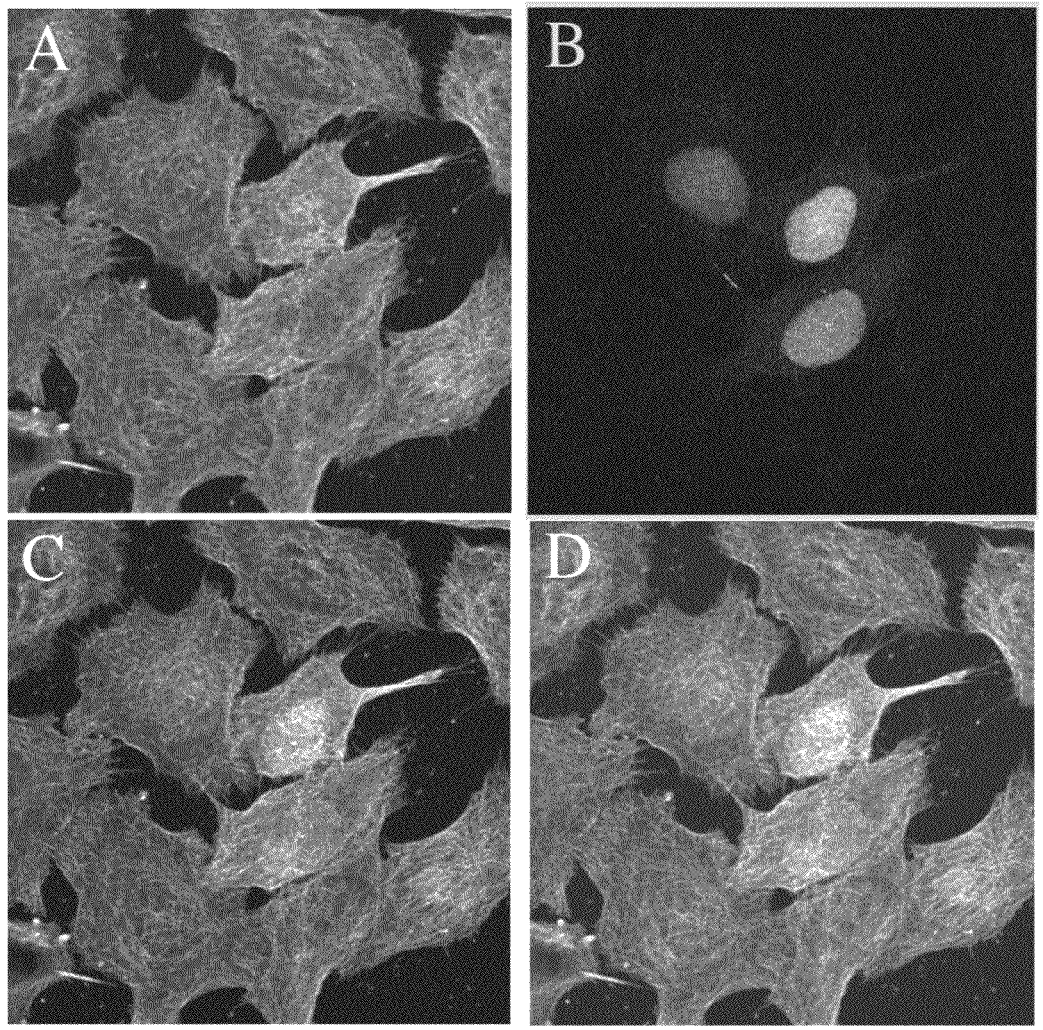
FIG. 8. Photomicrographs of double staining of HeLa cells using an intrabody and by immunofluorescence. HeLa cells were transfected with anti-histones clone 5 (FIG. 6) fused to the dsRed-monomer GFP. Microtubules were revealed in the transfected cells by IF using the anti-tubulin scFv 2F12C (Table 3). Cells were observed at the appropriate wavelength to visualize: (A) 2F12C scFv (microtubules alone); (B) clone 5 intrabody (histones alone); (C) 2F12C and clone 5 (both microtubules and histones); (D) as C plus nucleus staining with DAPI.

Sequences of the CDR3s of the best positive clones in an ELISA using cytoplasmically expressed scFv from the 2nd (5 clones) and the 3rd (6 clones) round of selection (Table 3).
[a]Frequency of apparition of the scFv among sequenced clones of the same round.
[b]Yield: mg of scFv purified from 1 liter of cells grown in a flask (OD$_{600}$ = 5).
[c]WB: detection of tubulin in brain extracts by Western blot.
[d]IF: + means that the scFv is able to reveal microtubule network by Immunofluorescence (FIG. 8).
The sequences of the clones 2C1C, 2E11C, 2F12C, 2G4C and 2G9C have been submitted to the EMBL database and their accession numbers are respectively AM886280, AM886281, AM886282, AM886283 and AM886284.

In all cases, the clones sequenced were those giving the best signal in the ELISA performed with cytoplasmically expressed scFvs. Most of the clones were different since only one clone from the 2nd round and one from the 3rd round were found twice. This demonstrated that a high diversity is still present after 3 rounds of selection. Eight of the anti-tubulin scFvs were purified by affinity chromatography from the cytoplasm. In all cases, more than 8 mg of scFv was purified from one liter of cells grown in a flask ($OD_{600}=5$), and some scFvs were expressed at a level per cell comparable to the exceptionally high expression level reported for an anti-HER2 in *E. coli* periplasm.

Functionality of scFvs as Intrabodies

Figure 6:
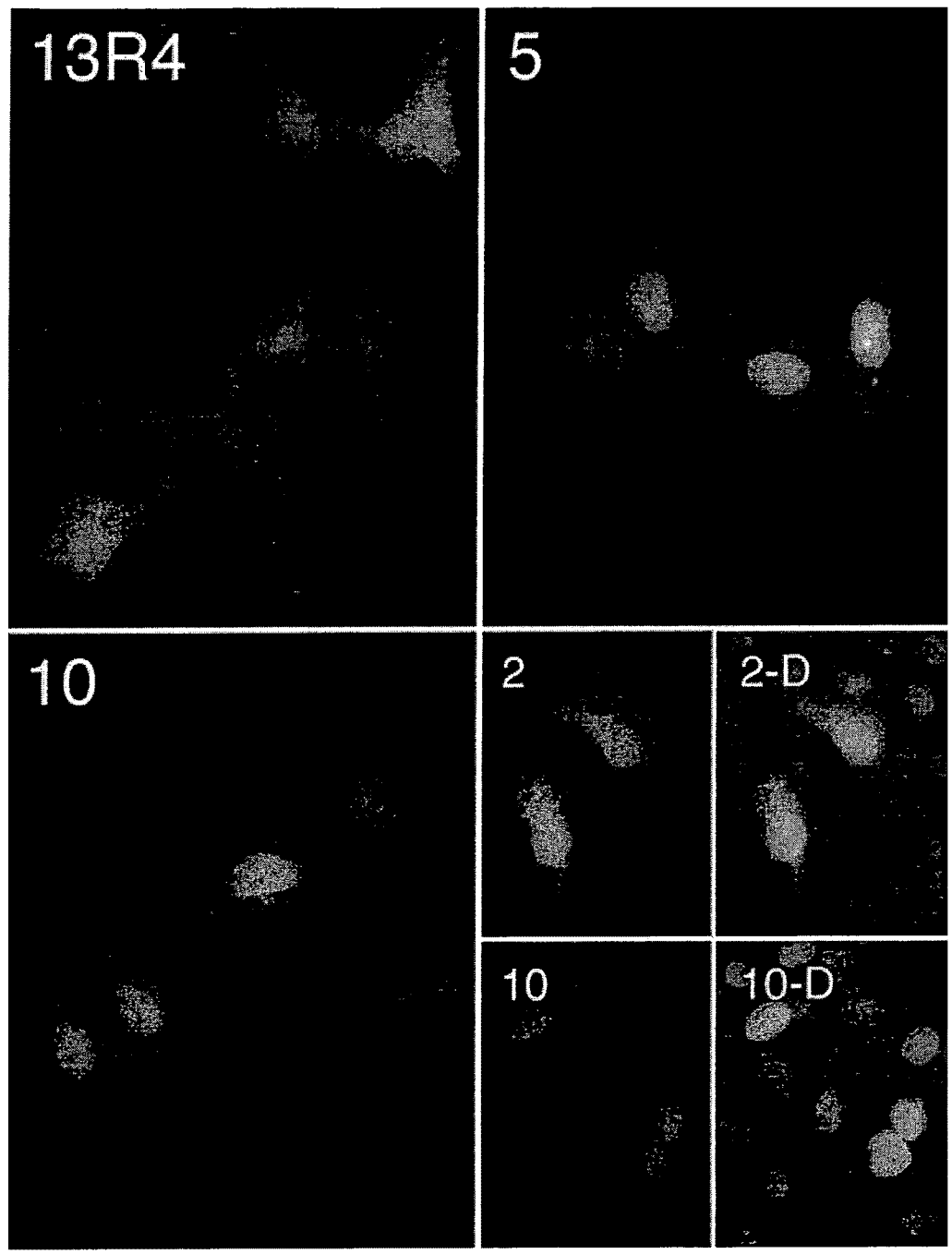
FIG. 6. Photomicrographs of the expression of anti-histones scFvs fused to EGFP in HeLa cells. The cells were transfected and treated as indicated in the legend of FIG. 4. The pictures represent typical cells transfected with scFv13R4 and three representative anti-histones clones (2, 5 and 10). D, DAPI staining (blue) merged with the GFP signal.

To determine if the isolated scFvs were able to bind to their target in vivo, the anti-histone scFvs expressed in human cells was characterized. The third round of selection was cloned in vector p513-EGFP and ten randomly chosen clones were transfected in HeLa cells. Typical results of the cells expressing the scFv-EGFP fusions and observed by fluorescence microscopy are shown in FIG. 6. One scFv was expressed as cytoplasmic aggregates. Four scFvs were expressed as soluble cytoplasmic proteins, as judged by the homogeneous staining of the cells, at a level comparable to that of the scFv13R4. Finally, the expression of three scFvs gave rise to a stronger staining of the nucleus (FIG. 6, clone 2) and two scFvs were exclusively localized in the nucleus (FIG. 6, clones 5 and 10). Since these scFvs-EGFP fusion proteins were expressed in the cytoplasm of the cell and did not contain a nuclear localization signal, this suggested that they were able to interact in vivo with the histones and were thus active inside the cell. This analysis showed that about half of the clones present after the third round of selection against core histones were able to bind to their nuclear target in vivo. This was confirmed in vitro by western and dot blot with purified scFv. In addition, sequencing of these clones showed that they contained different heavy and light chain CDR3 regions.

In Vitro Characterization of Anti-Tubulin scFvs

To demonstrate the activity of the anti-tubulin scFv under the reducing conditions in the cell cytoplasm, the scFvs were extracted in the presence of a reducing agent and compared the ELISA signal with that obtained with the scFvs extracted under oxidizing conditions. As shown in FIG. 7, the five scFvs tested gave the same ELISA signal under both conditions, demonstrating that the scFVs retain full activity under reducing conditions even in the absence of disulfide bond formation. The five scFvs were able to recognize unfolded tubulin by western blot in brain extracts and the native protein in a competition ELISA. The ability of the five scFvs to interact with microtubules in cells was tested by IF. Clones 2F 12C and 2G4C revealed the microtubule network in cells.

FIG. 8 illustrates the utility of the library as a source for both in vitro and in vivo proteomic studies: HeLa cells were transfected with the anti-histones clone 5 fused to a Red-GFP, and the microtubule network was revealed by IF using the 2F12C scFv.

Altogether our results show that the library described in this report is highly diverse and functional and allows fast and easy isolation of in vivo active fully human intrabodies.

All patents, publications and abstracts cited above are incorporated herein by reference in their entirety. Although only a few embodiments of the present invention have been described herein, it should be understood that the present invention can be embodied in many other specific forms without departing from the spirit or scope of the invention as claimed herein. Accordingly, the present examples and embodiments are to be considered as illustrative and not restrictive, and the invention is not to be limited to the details given herein.

What is claimed is:

1. A method for preparing an scFv antibody library comprising at least about $10^6$ unique scFv antibody clones, wherein the scFv antibody library is enriched for scFv antibody clones coding for scFv antibodies that are properly folded when expressed within the periplasm and/or cytoplasm of a prokaryote cell or within the cytoplasm of a mammalian cell, the method comprising:
   a) providing a first collection of scFv antibody clones derived from the scFv13R4 antibody nucleotide sequence of SEQ ID NO: 32, said collection of clones comprising a collection of unique sequences within the CDR3 loop of VH, step (a) comprising:
   (i) providing the following thirteen mixtures of spiked/degenerate oligonucleotides coding for random VH CDR3 sequences:

```
H3_5                                    (SEQ ID NO: 1)
AGGGTGCCTCTGCCCCA N(40/5/50/5) N(5/5/5/85)
N(60/5/25/10) N(40/10/45/5) N(15/30/5/50)
N(5/75/10/10) N(30/35/30/5) N(50/20/10/20)
```

-continued
N(60/20/5/15) N(30/25/40/5) N(15/20/25/40)
N(35/40/5/20) N(25/50/20/5) N(10/50/30/30)
N(5/55/35/5)
TCTCACACAGTAATAAACAGCCG, H3_6                                              (SEQ ID NO: 2)
AGGGTGCCTCTGCCCCA N(55/5/35/5) N(10/5/5/80)
N(75/15/5/5) N(45/5/45/5) N(5/10/10/75)
N(5/85/5/5) N(45/35/15/5) N(55/20/10/15)
N(55/20/10/15) N(40/30/25/5) N(10/40/15/35)
N(25/45/5/25) N(45/30/20/5) N(15/40/20/25)
N(10/35/30/25) N(20/15/60/5) N(10/60/10/20)
N(5/70/10/15) TCTCACACAGTAATAAACAGCCG, H3_7                                              (SEQ ID NO: 3)
AGGGTGCCTCTGCCCCA N(35/5/55/5) N(15/5/15/65)
N(65/15/10/10) N(55/5/35/5) N(5/5/5/85)
N(5/85/5/5) N(50/5/40/5) N(75/5/10/10)
N(60/10/20/10) N(10/45/40/5) N(15/35/25/25)
N(25/55/5/15) N(35/35/25/5) N(10/45/15/30)
N(25/45/15/15) N(25/25/25/25) N(20/40/15/25)
N(10/35/25/30) N(40/15/40/5) N(5/50/15/30)
N(5/80/10/5) TCTCACACAGTAATAAACAGCCG, H3_8                                              (SEQ ID NO: 4)
AGGGTGCCTCTGCCCCA N(55/5/35/5) N(10/5/10/75)
N(75/10/5/10) N(50/5/40/5) N(5/5/5/85) N(5/85/5/5)
N(45/5/45/5) N(75/5/10/10) N(65/5/20/10)
N(25/45/25/5) N(10/25/40/25) N(30/45/5/20)
N(55/10/30/5) N(5/55/15/25) N(5/55/15/25)
N(35/35/25/5) N(15/45/20/20) N(15/40/10/35)
N(30/40/25/5) N(20/35/20/25) N(15/40/20/25)
N(65/5/20/10) N(15/45/5/35) N(5/70/15/10)
TCTCACACAGTAATAAACAGCCG, H3_9                                              (SEQ ID NO: 5)
AGGGTGCCTCTGCCCCA N(40/5/50/5) N(10/5/10/75)
N(75/5/15/5) N(40/5/50/5) N(5/5/5/85) N(5/85/5/5)
N(45/5/45/5) N(85/5/5/5) N(70/5/15/10)
N(55/25/15/5) N(10/25/35/30) N(35/45/15/5)
N(10/25/60/5) N(10/35/20/35) N(20/45/15/20)
N(30/30/35/5) N(15/40/20/25) N(20/40/15/25)
N(65/20/10/5) N(20/40/20/20) N(5/45/15/35)
N(15/30/50/5) N(20/45/20/15) N(5/40/25/30)
N(30/25/40/5) N(10/40/10/40) N(5/60/20/15)
TCTCACACAGTAATAAACAGCCG, H3_10                                             (SEQ ID NO: 6)
AGGGTGCCTCTGCCCCA N(50/5/40/5) N(20/5/10/65)
N(70/10/15/5) N(60/5/30/5) N(5/5/5/85) N(5/85/5/5)
N(35/5/55/5) N(85/5/5/5) N(75/5/15/5) N(30/35/30/5)
N(10/20/45/25) N(30/45/15/10) N(30/35/30/5)
N(5/30/20/45) N(30/40/10/20) N(40/35/20/5)
N(15/35/25/25) N(25/35/15/25) N(50/30/15/5)
N(10/45/20/25) N(20/50/10/20) N(25/20/50/5)
N(20/40/20/20) N(5/50/15/30) N(20/20/40/20)
N(20/35/20/25) N(5/35/30/30) N(5/30/60/5)
N(15/35/10/40) N(5/60/15/20)
TCTCACACAGTAATAAACAGCCG, H3_11                                             (SEQ ID NO: 7)
AGGGTGCCTCTGCCCCA N(55/5/35/5) N(10/5/10/75)
N(80/5/10/5) N(60/5/30/5) N(5/5/5/85) N(5/85/5/5)
N(45/5/45/5) N(85/5/5/5) N(75/10/10/5)
N(40/30/25/5) N(10/20/35/35) N(35/35/20/10)
N(40/30/25/5) N(10/25/20/45) N(35/35/15/15)
N(35/30/30/5) N(15/30/25/30) N(35/30/15/20)
N(20/35/40/5) N(20/35/25/20) N(30/40/10/20)
N(5/35/50/10) N(20/30/20/30) N(30/40/15/15)
N(35/35/5/5) N(20/25/20/25) N(20/40/15/25)
N(45/25/10/20) N(20/35/20/25) N(20/30/25/25)
N(45/25/5/25) N(15/35/10/40) N(5/60/20/15)
TCTCACACAGTAATAAACAGCCG, H3_12                                             (SEQ ID NO: 8)
AGGGTGCCTCTGCCCCA N(45/5/45/5) N(15/5/15/65)
N(70/5/15/10) N(40/5/50/5) N(5/5/5/85) N(5/85/5/5)
N(45/5/45/5) N(85/5/5/5) N(75/5/15/5) N(10/30/55/5)
N(10/30/25/35) N(40/40/15/5) N(25/25/45/5)
N(10/25/20/45) N(35/35/10/20) N(40/40/15/5)
N(20/20/35/25) N(40/30/15/15) N(10/40/45/5)

-continued
N(20/25/30/25) N(35/35/15/15) N(30/30/35/5)
N(15/40/20/25) N(20/45/5/30) N(15/25/40/20)
N(20/30/25/25) N(20/40/15/25) N(15/25/40/20)
N(20/35/20/25) N(25/40/15/20) N(50/30/15/5)
N(20/45/20/15) N(5/35/35/25) N(45/25/25/5)
N(15/35/10/40) N(5/65/15/15)
TCTCACACAGTAATAAACAGCCG, H3_13                                             (SEQ ID NO: 9)
AGGGTGCCTCTGCCCCA N(45/10/40/5) N(15/5/15/65)
N(75/5/15/5) N(35/5/55/5) N(5/5/5/85) N(5/85/5/5)
N(45/5/45/5) N(85/5/5/5) N(80/5/10/5) N(35/25/35/5)
N(10/30/25/35) N(40/45/10/5) N(15/25/55/5)
N(10/25/15/55) N(35/35/10/20) N(55/30/10/5)
N(15/20/25/40) N(45/25/10/20) N(25/30/40/5)
N(20/30/20/30) N(30/35/15/20) N(15/25/55/5)
N(15/35/20/30) N(25/45/10/20) N(10/45/40/5)
N(20/25/25/30) N(30/40/10/20) N(30/25/30/15)
N(20/25/25/30) N(35/35/15/15) N(25/30/30/15)
N(20/30/20/30) N(25/35/20/20) N(40/30/25/5)
N(20/45/20/15) N(5/35/35/25) N(45/25/25/5)
N(15/35/15/40) N(5/65/20/10)
TCTCACACAGTAATAAACAGCCG, H3_14                                             (SEQ ID NO: 10)
AGGGTGCCTCTGCCCCA N(50/5/40/5) N(20/5/15/60)
N(60/10/25/5) N(35/5/55/5) N(5/5/5/85) N(5/85/5/5)
N(30/20/45/5) N(85/5/5/5) N(80/5/5/10) N(30/35/30/5)
N(10/35/20/35) N(40/40/15/5) N(50/25/20/5)
N(10/25/10/55) N(40/30/10/20) N(20/20/55/5)
N(15/20/20/45) N(45/25/15/15) N(15/25/55/5)
N(15/30/25/30) N(35/30/15/20) N(40/30/25/5)
N(15/25/25/35) N(35/10/20) N(20/30/40/10)
N(15/30/25/25) N(25/40/10/25) N(50/25/15/10)
N(15/35/25/25) N(35/35/10/20) N(15/35/45/15)
N(15/30/25/30) N(35/35/10/20) N(15/30/40/15)
N(20/30/20/30) N(30/40/10/20) N(30/30/15/25)
N(20/35/25/20) N(20/30/30/20) N(30/25/40/5)
N(10/30/15/45) N(5/70/15/10)
TCTCACACAGTAATAAACAGCCG, H3_15                                             (SEQ ID NO: 11)
AGGGTGCCTCTGCCCCA N(30/5/45/20) N(45/5/5/45)
N(45/35/5/15) N(45/45/5/5) N(5/5/5/85) N(5/85/5/5)
N(45/20/30/5) N(85/5/5/5) N(85/5/5/5) N(20/35/40/5)
N(5/40/25/30) N(35/50/10/5) N(15/5/75/5)
N(10/10/20/60) N(50/30/10/10) N(25/10/55/10)
N(15/20/20/45) N(50/25/15/10) N(35/30/30/5)
N(15/25/25/35) N(50/20/15/15) N(35/5/35/25)
N(10/30/30/30) N(35/35/10/20) N(20/40/35/5)
N(20/20/35/25) N(35/35/15/15) N(45/35/15/5)
N(15/30/25/30) N(35/35/10/20) N(35/25/25/5)
N(20/20/30/30) N(30/35/15/20) N(30/25/40/5)
N(15/30/20/35) N(35/30/15/20) N(35/25/35/5)
N(15/35/20/30) N(25/35/25/15) N(5/30/45/20)
N(20/20/35/25) N(15/30/30/25) N(45/25/25/5)
N(15/35/10/40) N(5/70/15/10)
TCTCACACAGTAATAAACAGCCG, H3_16                                             (SEQ ID NO: 12)
AGGGTGCCTCTGCCCCA N(35/10/30/25) N(65/5/5/25)
N(25/55/5/15) N(45/5/45/5) N(5/5/5/85) N(5/85/5/5)
N(35/30/30/5) N(85/5/5/5) N(75/5/5/15)
N(15/35/45/5) N(5/45/20/30) N(35/55/5/5)
N(50/5/40/5) N(10/5/15/70) N(60/20/10/10)
N(65/5/25/5) N(10/10/25/55) N(55/15/15/15)
N(30/5/60/5) N(10/15/30/45) N(55/15/15/15)
N(25/25/45/5) N(20/20/15/35) N(40/35/10/15)
N(40/20/30/10) N(15/35/25/25) N(35/30/10/25)
N(45/30/15/10) N(15/35/25/25) N(30/25/10/25)
N(35/30/25/10) N(20/25/30/25) N(35/35/10/20)
N(30/20/30/20) N(20/35/20/25) N(30/40/10/20)
N(45/20/20/15) N(20/20/25/35) N(30/35/15/20)
N(45/30/20/5) N(15/35/25/25) N(25/35/20/20)
N(40/15/5/40) N(20/35/20/25) N(15/30/25/30)
N(30/30/35/5) N(15/30/15/40) N(5/75/15/5)
TCTCACACAGTAATAAACAGCCG, and -continued H3_17 (SEQ ID NO: 13)
AGGGTGCCTCTGCCCCA N(45/10/20/25) N(70/5/5/20)
N(15/60/5/20) N(40/5/50/5) N(5/5/5/85) N(5/85/5/5)
N(25/20/50/5) N(85/5/5/5) N(80/5/5/10)
N(10/45/40/5) N(5/50/20/25) N(30/60/5/5)
N(5/5/85/5) N(5/5/15/75) N(65/20/5/10)
N(45/5/45/5) N(10/10/20/60) N(55/10/20/15)
N(45/5/45/5) N(15/15/20/50) N(60/15/15/10)
N(60/20/15/5) N(10/30/20/40) N(45/25/15/15)
N(15/35/45/5) N(15/15/35/35) N(40/30/15/15)
N(30/25/40/5) N(20/30/25/25) N(30/35/10/25)
N(20/30/40/10) N(15/35/25/25) N(30/35/10/25)
N(40/30/25/5) N(20/30/25/25) N(40/35/10/15)
N(35/20/40/5) N(20/25/20/35) N(40/35/10/15)
N(35/20/40/5) N(20/20/20/40) N(35/35/15/15)
N(30/20/30/20) N(20/30/20/30) N(25/30/25/20)
N(35/35/25/5) N(25/35/20/20) N(5/35/40/20)
N(20/30/45/5) N(15/30/10/45) N(5/70/15/10)
TCTCACACAGTAATAAACAGCCG, wherein for the degenerate position (N) the molar percentage of the bases are given as N(A/C/G/T);

(ii) producing thirteen independent libraries of scFv13R4 antibody clones with degenerate VH CDR3 sequences by replacing the corresponding VH CDR3 sequence of scFv13R4 antibody nucleotide sequence SEQ ID NO: 32 by the thirteen mixtures of spiked/degenerate oligonucleotides coding for random VH CDR3 sequences of step (a)(i), wherein the VH CDR3 coding sequence of the produced scFv13R4 antibody clones is linked to a sequence encoding a first selectable marker so that the encoded scFv13R4 antibody with degenerate VH CDR3 sequences is fused to the first selectable marker;

(iii) inserting each of the thirteen independent libraries of scFv13R4 antibody clones with the degenerate VH CDR3 sequences obtained in step (a)(ii) into an appropriate prokaryote or mammalian cell, and then culturing said cells in the presence of a substance suitable for assessing whether the first selectable marker is expressed and functional within the periplasm and/or cytoplasm of the prokaryote cell or within the cytoplasm of the mammalian cell;

(iv) selecting from each of the thirteen independent libraries of scFv13R4 antibody clones with degenerate VH CDR3 sequences the clones which express a functional first selectable marker fused to the scFv antibody;

(v) pooling the scFv13R4 antibody clones of the thirteen independent libraries with degenerate VH CDR3 sequences selected in step (a)(iv), the pool of selected clones constituting a first collection of scFv antibody clones derived from the scFv13R4 antibody nucleotide sequence SEQ ID NO: 32;

b) providing a second collection of scFv antibody clones derived from the scFv13R4 antibody clone of SEQ ID NO: 32, said collection of clones comprising a collection of unique sequences within the CDR3 loop of VL, step (b) comprising:

(i) providing the following five mixtures of spiked/degenerate oligonucleotides coding for random VL CDR3 sequences:

```
K3_9                                            (SEQ ID NO: 14)
GGACGAGGCTGATTATTACTGC N(5/85/5/5) N(85/5/5/5)
N(5/5/85/5) N(5/85/5/5) N(85/5/5/5) N(40/5/50/5)
N(5/5/10/80) N(65/25/5/5) N(5/50/5/40)
N(30/5/25/40) N(60/10/20/10) N(5/40/10/45)
N(80/5/10/5) N(30/15/50/5) N(5/60/5/30)
N(35/5/10/50) N(30/40/10/20) N(5/15/45/35)
```

-continued

```
N(5/85/5/5) N(5/85/5/5) N(5/5/85/5) N(5/40/5/50)
N(30/10/25/35) N(5/35/50/10) N(85/5/5/5)
N(5/85/5/5) N(5/50/30/15) TTCGGCGGAGGGACCAAG,

K3_10                                           (SEQ ID NO: 15)
GGACGAGGCTGATTATTACTGC N(5/85/5/5) N(85/5/5/5)
N(5/5/85/5) N(5/85/5/5) N(85/5/5/5) N(40/5/50/5)
N(5/5/5/85) N(80/10/5/5) N(25/20/5/50)
N(35/5/40/20) N(45/5/45/5) N(5/30/15/50)
N(75/10/10/5) N(40/5/50/5) N(5/45/5/45)
N(20/5/5/70) N(10/45/40/5) N(5/5/85/5)
N(5/85/5/5) N(5/85/5/5) N(5/5/85/5) N(5/85/5/5)
N(5/65/15/15) N(5/5/85/5) N(15/5/10/70)
N(20/5/30/45) N(5/30/50/15) N(85/5/5/5)
N(5/85/5/5) N(5/40/5/50) TTCGGCGGAGGGACCAAG,

L3_9                                            (SEQ ID NO: 16)
GGACGAGGCTGATTATTACTGC N(5/85/5/5) N(80/5/5/10)
N(5/5/85/5) N(20/5/30/45) N(5/75/5/15) N(85/5/5/5)
N(5/5/5/85) N(35/5/55/5) N(5/10/80/5) N(5/10/80/5)
N(80/10/5/5) N(5/60/5/30) N(65/5/25/5)
N(15/10/70/5) N(5/65/5/25) N(70/5/20/5)
N(20/10/65/5) N(5/60/5/30) N(65/10/20/5)
N(15/45/20/20) N(5/40/10/45) N(15/5/50/30)
N(10/15/25/50) N(5/20/70/5) N(10/5/80/5)
N(5/5/5/85) N(5/40/10/45) TTCGGCGGAGGGACCAAG,

L3_10                                           (SEQ ID NO: 17)
GGACGAGGCTGATTATTACTGC N(45/5/10/40) N(15/15/60/10)
N(10/50/5/35) N(5/5/5/85) N(5/85/5/5) N(45/5/45/5)
N(5/5/5/85) N(85/5/5/5) N(5/50/5/40) N(25/5/65/5)
N(45/45/5/5) N(5/45/5/45) N(55/5/35/5)
N(10/10/75/5) N(5/40/5/50) N(85/5/5/5)
N(15/10/70/5) N(5/50/5/40) N(70/5/20/5)
N(30/20/45/5) N(5/75/5/15) N(70/15/10/5)
N(25/45/15/15) N(5/35/5/55) N(5/15/35/45)
N(15/5/30/50) N(5/15/75/5) N(10/5/80/5)
N(5/5/5/85) N(5/50/10/35) TTCGGCGGAGGGACCAAG, and L3_11                                           (SEQ ID NO: 18)
GGACGAGGCTGATTATTACTGC N(10/55/25/10) N(65/20/10/5)
N(5/10/80/5) N(20/5/20/55) N(5/85/5/5) N(5/5/85/5)
N(5/5/5/85) N(30/5/60/5) N(5/5/85/5) N(5/5/85/5)
N(85/5/5/5) N(5/45/5/45) N(75/5/15/5)
N(20/10/65/5) N(5/60/5/30) N(85/5/5/5) N(5/5/85/5)
N(5/35/5/55) N(5/5/5/85) N(5/30/10/55) N(85/5/5/5)
N(75/5/15/5) N(45/20/30/5) N(5/20/5/70)
N(5/30/50/15) N(25/25/35/15) N(5/45/15/35)
N(10/5/50/35) N(20/5/25/50) N(5/20/60/15)
N(5/5/85/5) N(5/5/5/85) N(70/5/20/5)
TTCGGCGGAGGGACCAAG,
``` wherein for the degenerate position (N) the molar percentage of the bases are given as N(A/C/G/T);

(ii) producing five independent libraries of scFv13R4 antibody clones with degenerate VL CDR3 sequences by replacing the corresponding VL CDR3 sequence of scFv13R4 antibody sequence SEQ ID NO: 32 by the five mixtures of spiked/degenerate oligonucleotides coding for random VL CDR3 sequences of step (b)(i), wherein the VL CDR3 coding sequence of the produced scFv13R4 antibody clones is linked to a sequence encoding a second selectable marker so that the encoded scFv13R4 antibody with degenerate VL CDR3 sequences is fused to the second selectable marker;

(iii) inserting each of the five independent libraries of scFv13R4 antibody clones with the degenerate VL CDR3 sequences obtained in step (b)(ii) into an appropriate prokaryote or mammalian cell, and then culturing said cells in the presence of a substance suitable for assessing whether the second selectable marker is expressed and functional within the periplasm and/or cytoplasm of the prokaryote cell or within the cytoplasm of the mammalian cell;

(iv) selecting from each of the five independent libraries of scFv13R4 antibody clones with degenerate VL CDR3 sequences the clones which express the second functional selectable marker fused to the scFv antibody;

(v) pooling the scFv13R4 antibody clones of the five independent libraries with degenerate VL CDR3 sequences selected in step (b)(iv), the pool of selected clones constituting a second collection of scFv antibody clones derived from the scFv13R4 antibody nucleotide sequence SEQ ID NO: 32; and c) joining VH domains from the scFv13R4 antibody clones of the first collection with VL domains from the scFv13R4 antibody clones of the second collection to obtain a third collection of scFv antibody clones, wherein the third collection contains scFv antibody clones comprising a collection of unique sequences within the CDR3 loop of VH and a collection of unique sequences within the CDR3 loop of VL, thereby preparing the scFv antibody library enriched for scFv antibodies that are properly folded when expressed within the periplasm and/or cytoplasm of a prokaryote cell or within the cytoplasm of a mammalian cell.

2. The method of claim 1, wherein the first collection comprises scFv13R4 antibody clones with degenerate VH CDR3 sequences that comprise identical CDR1 and CDR2 sequences in the VH domain, and wherein the second collection comprises scFv13R4 antibody clones with degenerate VL CDR3 sequences that comprise identical CDR1 and CDR2 sequences in the VL domain.

3. An antibody library produced by the method of claim 1.

4. The method of claim 1, wherein the first selectable marker and second selectable marker is a gene encoding chloramphenicol acetyltransferase (CAT), and the substance suitable for assessing whether the first and second selectable marker are expressed and functional is chloramphenicol.

5. The method of claim 1, wherein in steps (a)(iii) and (b)(iii), the libraries of scFv13R4 antibody clones are inserted into *Escherichia coli* cells.

6. An antibody library produced by the method of claim 4.

* * * * *